United States Patent
Donofrio et al.

(10) Patent No.: US 7,328,131 B2
(45) Date of Patent: Feb. 5, 2008

(54) IMPLANTABLE PEDOMETER

(75) Inventors: William T. Donofrio, Andover, MN (US); Jeffrey H. Nycz, Collierville, TN (US); Sarah Anne Audet, Shoreview, MN (US); Can Cinbis, Shoreview, MN (US); Michael A. Schugt, St. Paul, MN (US); Gerard J. Hill, Champlin, MN (US); Qingshan (Sam) Ye, Plymouth, MN (US)

(73) Assignees: Medtronic, Inc., Minneapolis, MA (US); Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 11/344,999

(22) Filed: Feb. 1, 2006

(65) Prior Publication Data

US 2007/0179739 A1   Aug. 2, 2007

(51) Int. Cl.
 *G06F 17/00* (2006.01)
(52) U.S. Cl. .......................... 702/183; 73/645; 73/763; 73/764; 340/539.12; 340/573.1; 340/870.01; 340/870.07; 377/1; 377/13; 600/552; 600/553; 600/586; 600/587; 702/127; 702/160; 702/182
(58) Field of Classification Search ............... 73/432.1, 73/570, 577, 584, 587, 645, 646, 760, 763, 73/764, 768, 774, 775, 865.1; 340/500, 531, 340/539.1, 539.11, 539.12, 573.1, 669, 870.01, 340/870.07; 377/1, 13, 15, 16; 702/33, 702/34, 41, 42, 127, 141, 160, 182, 183; 600/552, 553, 586, 587
See application file for complete search history.

(56) References Cited

U.S. PATENT DOCUMENTS

| 3,181,528 | A | * | 5/1965 | Brackin ................ 600/586 |
| 4,195,367 | A |   | 4/1980 | Kraus |
| 4,195,643 | A | * | 4/1980 | Pratt, Jr. .............. 600/592 |
| 4,246,791 | A |   | 1/1981 | Glenn |
| 4,430,999 | A |   | 2/1984 | Brighton et al. |
| 4,519,394 | A |   | 5/1985 | Black et al. |
| 4,669,482 | A |   | 6/1987 | Ophir |
| 4,781,181 | A |   | 11/1988 | Tanguy |
| 4,813,435 | A |   | 3/1989 | Arms |
| 4,993,428 | A |   | 2/1991 | Arms |

(Continued)

FOREIGN PATENT DOCUMENTS

DE   103 42 823 A1 *   4/2005

(Continued)

OTHER PUBLICATIONS

U.S. Appl. No. 11/344,677, filed Feb. 1, 2006, inventor Donofrio et al.

(Continued)

Primary Examiner—Edward R Cosimano
(74) Attorney, Agent, or Firm—Haynes Boone, LLP

(57) ABSTRACT

An implantable pedometer for measuring the amount of joint use is disclosed. The implantable pedometer includes a sensor adapted for detecting indicators of joint usage. A counter is configured for storing count data corresponding to the number of indicators detected by the sensor and a telemetry circuit is configured for transmitting the count data outside of the body.

49 Claims, 10 Drawing Sheets

U.S. PATENT DOCUMENTS

| | | |
|---|---|---|
| 5,038,787 A | 8/1991 | Antich et al. |
| 5,083,573 A | 1/1992 | Arms |
| 5,125,408 A | 6/1992 | Basser |
| 5,197,475 A | 3/1993 | Antich et al. |
| 5,197,488 A | 3/1993 | Kovacevic |
| 5,289,826 A | 3/1994 | Kovacevic |
| 5,306,306 A | 4/1994 | Bisek et al. |
| 5,360,016 A | 11/1994 | Kovacevic |
| 5,402,781 A | 4/1995 | Dimarogonas |
| 5,413,116 A * | 5/1995 | Radke et al. ............... 600/590 |
| 5,425,775 A | 6/1995 | Kovacevic et al. |
| 5,456,724 A | 10/1995 | Yen et al. |
| 5,470,354 A | 11/1995 | Hershberger et al. |
| 5,480,439 A | 1/1996 | Bisek et al. |
| 5,533,519 A * | 7/1996 | Radke et al. ............... 600/595 |
| 5,564,423 A | 10/1996 | Mele et al. |
| 5,590,658 A | 1/1997 | Chiang et al. |
| 5,610,966 A | 3/1997 | Martell et al. |
| 5,690,114 A | 11/1997 | Chiang et al. |
| 5,694,946 A | 12/1997 | Tenerz et al. |
| 5,695,496 A | 12/1997 | Orsak et al. |
| 5,749,363 A | 5/1998 | Ishii et al. |
| 5,810,735 A | 9/1998 | Halperin et al. |
| 5,836,876 A | 11/1998 | Dimarogonas |
| 5,839,442 A | 11/1998 | Chiang et al. |
| 5,852,647 A | 12/1998 | Schick et al. |
| 5,853,005 A | 12/1998 | Scanlon |
| 5,891,033 A | 4/1999 | O'Neill et al. |
| 5,935,171 A | 8/1999 | Schneider et al. |
| 5,957,846 A | 9/1999 | Chiang et al. |
| 5,964,709 A | 10/1999 | Chiang et al. |
| 6,034,296 A | 3/2000 | Elvin et al. |
| 6,059,784 A | 5/2000 | Perusek |
| 6,074,394 A | 6/2000 | Krause |
| 6,106,472 A | 8/2000 | Chiang et al. |
| 6,200,266 B1 | 3/2001 | Shokrollahi et al. |
| 6,230,036 B1 | 5/2001 | O'Neill et al. |
| 6,235,038 B1 | 5/2001 | Hunter et al. |
| 6,241,673 B1 | 6/2001 | Williams et al. |
| 6,245,109 B1 * | 6/2001 | Mendes et al. .......... 623/18.11 |
| 6,292,680 B1 | 9/2001 | Somogyi et al. |
| 6,364,849 B1 | 4/2002 | Wilcox |
| 6,433,629 B2 | 8/2002 | Hamel et al. |
| 6,436,042 B1 | 8/2002 | Cadossi et al. |
| 6,447,448 B1 * | 9/2002 | Ishikawa et al. ............ 600/300 |
| 6,503,249 B1 | 1/2003 | Krause |
| 6,529,127 B2 | 3/2003 | Townsend et al. |
| 6,537,233 B1 | 3/2003 | Rangayyan et al. |
| 6,540,685 B1 | 4/2003 | Rhoads et al. |
| 6,544,749 B1 | 4/2003 | Kim |
| 6,573,706 B2 | 6/2003 | Mendes et al. |
| 6,583,630 B2 | 6/2003 | Mendes et al. |
| 6,585,647 B1 | 7/2003 | Winder |
| 6,610,096 B2 | 8/2003 | MacDonald |
| 6,610,101 B2 | 8/2003 | Herr et al. |
| 6,621,278 B2 | 9/2003 | Ariav |
| 6,628,989 B1 | 9/2003 | Penner et al. |
| 6,656,135 B2 * | 12/2003 | Zogbi et al. ............... 600/594 |
| 6,676,291 B2 | 1/2004 | Ahn |
| 6,692,450 B1 | 2/2004 | Coleman |
| 6,695,885 B2 | 2/2004 | Schulman et al. |
| 6,706,005 B2 | 3/2004 | Roy et al. |
| 6,706,071 B1 | 3/2004 | Wolter |
| 6,761,741 B2 | 7/2004 | Iesaka |
| 6,821,299 B2 | 11/2004 | Kirking et al. |
| 6,849,463 B2 | 2/2005 | Santini et al. |
| 6,856,141 B2 | 2/2005 | Ariav |
| 6,889,165 B2 | 5/2005 | Lind et al. |
| 6,899,680 B2 | 5/2005 | Hoff et al. |
| 6,918,308 B2 | 7/2005 | Biedermann et al. |
| 6,980,419 B2 | 12/2005 | Smith et al. |
| 6,984,993 B2 | 1/2006 | Ariav |
| 2002/0024450 A1 | 2/2002 | Townsend et al. |
| 2002/0103435 A1 | 8/2002 | Mault |
| 2002/0107649 A1 | 8/2002 | Takiguchi et al. |
| 2002/0133094 A1 | 9/2002 | Wilcox et al. |
| 2002/0198526 A1 | 12/2002 | Shaolian et al. |
| 2003/0069644 A1 | 4/2003 | Kovacevic et al. |
| 2003/0120150 A1 | 6/2003 | Govari |
| 2003/0139690 A1 | 7/2003 | Aebli et al. |
| 2003/0167002 A1 | 9/2003 | Nagar et al. |
| 2003/0199783 A1 | 10/2003 | Bloom et al. |
| 2004/0011137 A1 | 1/2004 | Hnat et al. |
| 2004/0021322 A1 | 2/2004 | Ariav |
| 2004/0054302 A1 | 3/2004 | Czernicki |
| 2004/0059423 A1 | 3/2004 | Barnes et al. |
| 2004/0068205 A1 | 4/2004 | Zogbi et al. |
| 2004/0113790 A1 | 6/2004 | Hamel et al. |
| 2004/0129095 A1 | 7/2004 | Churchill et al. |
| 2004/0143186 A1 | 7/2004 | Anisimov et al. |
| 2004/0143302 A1 | 7/2004 | Sieracki et al. |
| 2004/0152972 A1 | 8/2004 | Hunter |
| 2004/0186396 A1 | 9/2004 | Roy et al. |
| 2004/0204647 A1 | 10/2004 | Grupp et al. |
| 2004/0204744 A1 | 10/2004 | Penner et al. |
| 2004/0207409 A1 | 10/2004 | Ariav et al. |
| 2004/0236192 A1 | 11/2004 | Necola et al. |
| 2004/0236221 A1 | 11/2004 | Wilcox et al. |
| 2005/0010299 A1 | 1/2005 | Disilvestro |
| 2005/0010300 A1 | 1/2005 | DiSilvestro et al. |
| 2005/0010301 A1 | 1/2005 | DiSilvestro et al. |
| 2005/0010302 A1 | 1/2005 | Dietz et al. |
| 2005/0012610 A1 | 1/2005 | Liao et al. |
| 2005/0012617 A1 | 1/2005 | Disilvestro et al. |
| 2005/0015010 A1 | 1/2005 | Antich et al. |
| 2005/0027192 A1 | 2/2005 | Govari et al. |
| 2005/0085725 A1 | 4/2005 | Nagar et al. |
| 2005/0099290 A1 | 5/2005 | Govari |
| 2005/0113691 A1 | 5/2005 | Liebschner |
| 2005/0165317 A1 | 7/2005 | Turner et al. |
| 2005/0197576 A1 | 9/2005 | Luo et al. |
| 2005/0234555 A1 | 10/2005 | Sutton et al. |
| 2005/0245821 A1 | 11/2005 | Govari et al. |
| 2005/0272990 A1 | 12/2005 | Ariav et al. |
| 2005/0288596 A1 | 12/2005 | Eigler et al. |
| 2005/0288604 A1 | 12/2005 | Eigler et al. |
| 2005/0288722 A1 | 12/2005 | Eigler et al. |
| 2006/0009856 A1 | 1/2006 | Sherman et al. |
| 2006/0030914 A1 | 2/2006 | Eggers et al. |
| 2006/0032314 A1 | 2/2006 | Hnat et al. |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036301 A1 | 2/2006 | Eggers et al. |
| 2006/0036323 A1 | 2/2006 | Carl et al. |
| 2006/0036324 A1 | 2/2006 | Sachs et al. |
| 2006/0047283 A1 | 3/2006 | Evan, III et al. |
| 2006/0052782 A1 | 3/2006 | Morgan et al. |
| 2006/0069447 A1 | 3/2006 | Disilvestro et al. |
| 2006/0087325 A1 | 4/2006 | Ariav et al. |

FOREIGN PATENT DOCUMENTS

| | | |
|---|---|---|
| EP | 0344770 | 12/1989 |
| EP | 0619101 | 10/1994 |
| EP | 1238630 | 9/2002 |
| EP | 1285640 | 2/2003 |
| EP | 1442715 | 8/2004 |
| WO | 92/17113 | 10/1992 |
| WO | 97/33513 | 9/1997 |
| WO | 03/048688 | 6/2003 |
| WO | 2005007025 | 1/2005 |

| | | |
|---|---|---|
| WO | 2005062719 | 7/2005 |
| WO | 2005-0120167 | 12/2005 |
| WO | 2006105098 | 10/2006 |

OTHER PUBLICATIONS

Notification of Transmittal of the International Search Report and the Written Opinion of the International Searching Authority, of the Declaration issued by the European Patent Office dated Jul. 4, 2007 (12 pages).

Notification of Transmittal of the International Search Report and the written Opinion of the International Searching Authority, of the Declaration issued by the European Patent Office dated May 7, 2007 (13 pages).

Notification of Transmittal of the International Search Report and the Written Opinion of the International Searching Authority, of the Declaration issued by the European Patent Office dated May, 25, 2007 (13 pages).

* cited by examiner

IMPLANTABLE PEDOMETER

FIELD OF THE INVENTION

The present invention is directed to improved instrumentation and methods for measuring the use of a joint. More particularly, in one aspect the present invention is directed to an implantable pedometer for assessing the extent of use of an artificial joint.

BACKGROUND OF THE INVENTION

The present invention relates to instrumentation and methods for measuring the amount of use of a joint in a skeletal system. The invention is useful as applied to natural joints and artificial implants. The invention may be applied to a wide variety and types of implants. The invention may have particularly useful application to joint prostheses including hip, knee, shoulder, ankle, wrist, jaw, and spinal prostheses. Joint prostheses are usually manufactured of durable materials such as metals, ceramics, or hard plastics and are affixed to articulating ends of the bones of the joint. Joint prostheses usually include an articulating surface composed of a material designed to minimize the friction between the components of the joint prostheses. For example, in a hip prosthesis the femoral component is comprised of a head (or ball) and a stem attached to the femur. The acetabular component is comprised of a cup (or socket) attached to the acetabulum and most often includes a polyethylene articulating surface. The ball-in-socket motion between the femoral head and the acetabular cup simulates the natural motion of the hip joint and the polyethylene surface helps to minimize friction during articulation of the ball and socket.

It has been shown that over time implants will begin to degrade due to normal wear of the implant. Extensive or excessive use of the implant further increases the likelihood of implant degradation. Implant degradation, in turn, may cause polyethylene wear debris and implant loosing that can result in numerous medical problems including, but not limited to, osteolytic lesions and the possibility of requiring revision surgery. Early detection of the signs of implant degradation could allow an orthopedic surgeon to treat the potential problem before it escalates to the point of causing harm to the patient or the need for revision surgery.

Patients that extensively use or place repetitive loads on their implants are more likely to have implant degradation. Therefore, for more active patients it is necessary to carefully monitor the degradation of the implant with frequent examinations. However, these examinations are usually expensive, inconvenient, and often add undesired x-ray exposure to the patient. Thus, it is desirable to perform these examinations only when the patient's activity and implant usage levels are sufficiently high so as to increase the likelihood of implant degradation.

Therefore, there remains a need for improved instrumentation and methods for measuring the amount of use of a joint.

SUMMARY OF THE INVENTION

In one aspect, the invention provides for an implantable pedometer for measuring the use of a joint in a skeletal system. The pedometer includes a sensor and a telemetry circuit. At least a portion of an external surface of the sensor is configured for bone engagement. The sensor is adapted for detecting indicators of joint use and storing a count data corresponding to the indicators detected. The telemetry circuit is configured for transmitting the count data outside of the skeletal system.

In another aspect, the present invention provides an implantable pedometer for measuring use of a joint in a skeletal system. The pedometer includes a sensor and a telemetry unit. The sensor is adapted for placement outside of an artificial joint implant, detecting indicators of joint use, and storing a count data corresponding to the indicators detected. The telemetry circuit is configured for transmitting the count data outside of the skeletal system.

In another aspect, the present invention provides an implantable pedometer for measuring use of a joint in a skeletal system. The pedometer includes a sensor and a telemetry unit. The sensor is adapted for detecting natural indicators of joint use and storing a count data corresponding to the natural indicators detected. The telemetry circuit is configured for transmitting the count data outside of the skeletal system.

In another aspect, the present invention provides a method of evaluating the use of a joint in a body. The method includes implanting a sensor into the body, where the sensor is adapted for detecting indicators associated with use of the joint and storing a usage data corresponding to the indicators detected; obtaining the usage data from the sensor; and analyzing the usage data to evaluate the use of the joint.

Further aspects, forms, embodiments, objects, features, benefits, and advantages of the present invention shall become apparent from the detailed drawings and descriptions provided herein.

DESCRIPTION OF THE ILLUSTRATED EMBODIMENTS

Figure 1:
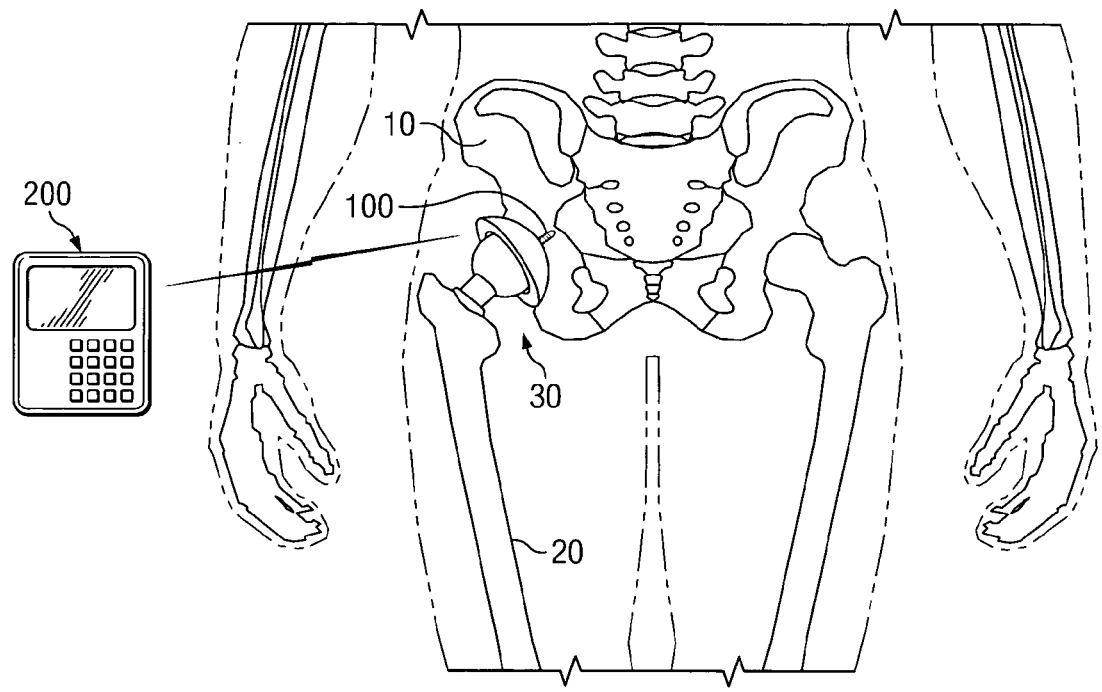
FIG. 1 is a front view of an implantable pedometer located adjacent to a hip prostheses in wireless communication with an external receiver according to one embodiment of the present invention.

For the purposes of promoting an understanding of the principles of the present invention, reference will now be made to the embodiments illustrated in the drawings, and specific language will be used to describe the same. It will nevertheless be understood that no limitation of the scope of the invention is intended. Any alterations and further modifications in the described devices, instruments, methods, and any further application of the principles of the invention as described herein are contemplated as would normally occur to one skilled in the art to which the invention relates.

Figure 2A:
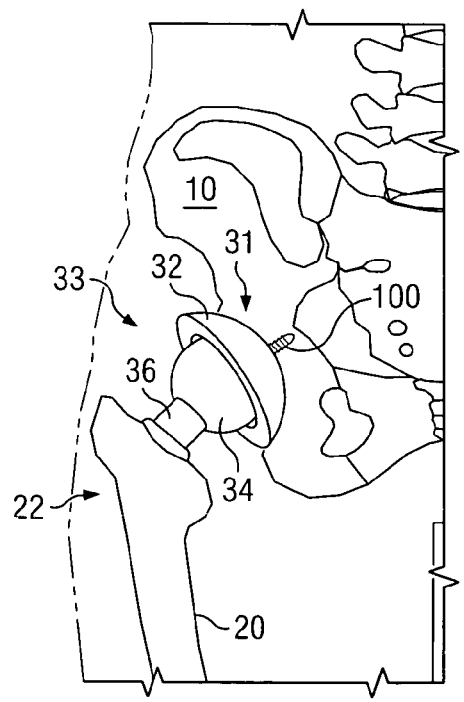
FIG. 2A is an enlarged front view of the implantable pedometer located adjacent to a hip prostheses shown in FIG. 1.
Figure 2B:
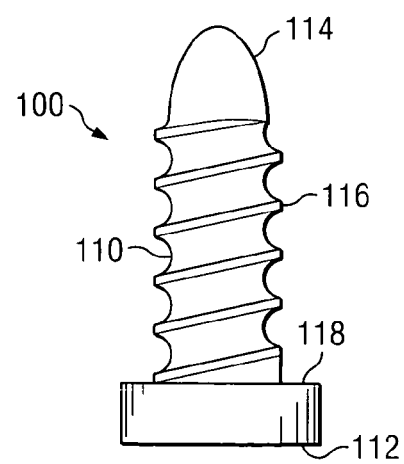
FIG. 2B is an enlarged side view of the implantable pedometer of FIG. 1.
Figure 2C:
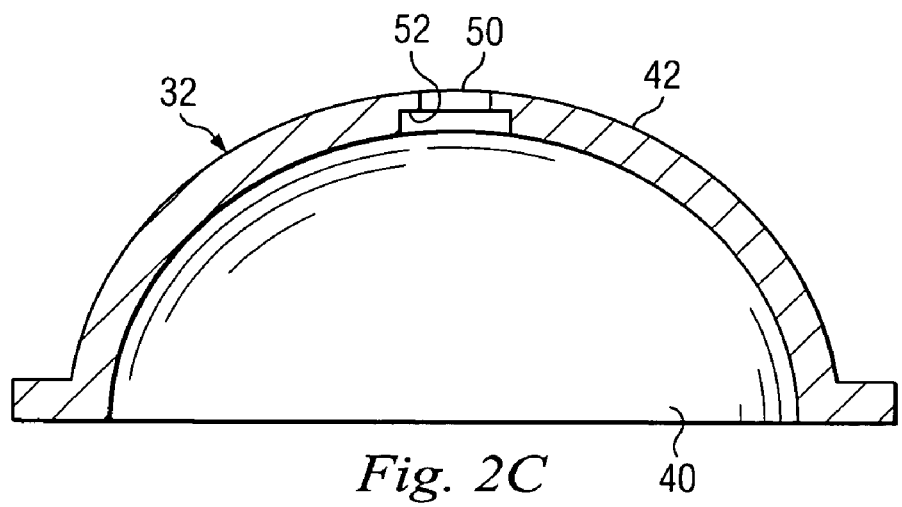
FIG. 2C is an enlarged cross-sectional side view of a portion of the hip prosthesis of FIG. 1.

Referring now to FIGS. 1, 2A, 2B, 2C, 2D, 3, and 4, there is shown a system for monitoring indicators associated with use of a hip implant or prostheses 30 according to one aspect of the present invention. The hip prosthesis 30 being monitored includes an acetabular component 31 and a femoral component 33. The acetabular component 31 comprises an acetabular cup 32 configured for engagement with a prepared portion of the patient's acetabulum 10. As shown in FIG. 2C, acetabular cup 32 includes an opening 50 adapted to engage an insertion tool for driving the cup into position. Opening 50 includes an internal flange 52 of reduced diameter. The acetabular cup also has a substantially spherical internal surface 40 and an exterior surface 42. The femoral component 33 comprises a head 34 and a stem 36.

The femoral head 34 is configured for movable engagement with the internal surface 40 of the acetabular cup 32 so as to create ball-in-socket motion. The stem 36 of the femoral component is adapted for engaging a proximal portion 22 of the patient's femur 20. The ball-in-socket motion between the femoral head 34 and the acetabular cup 32 simulates the natural motion of the patient's hip joint.

FIG. 1 shows an implantable pedometer 100 in wireless communication with an external receiver 200. The implantable pedometer 100 is configured to detect and keep track of indicators associated with the usage of a joint. In one aspect, the natural hip joint has been replaced by an artificial hip implant 30. The implantable pedometer 100 is also configured for wireless communication with the external receiver 200. Similarly, the external receiver 200 is configured for wireless communication with the implantable pedometer 100. In particular, the external receiver 200 is adapted for retrieving and displaying, in human intelligible form, the implant usage data kept by the implantable pedometer 100.

In the illustrated embodiment, the implantable pedometer 100 is disposed adjacent to the acetabular cup 32 of the hip implant 30. As discussed more fully below, it is fully contemplated that the pedometer 100 may be disposed at a plurality of locations including within or integral to an artificial joint, adjacent to the joint, near the joint, or distal to the joint. In the current embodiment the pedometer 100 is disposed adjacent the hip implant 30. As illustrated, the pedometer 100 is positioned adjacent the acetabular cup 32. However, the pedometer 100 may also be disposed adjacent the femoral stem 36 of the hip implant 30. There are a plurality of other locations for the pedometer 100 adjacent to the hip implant 30 that are adequate for monitoring use of the hip implant 30. The precise locations available for placement of the pedometer 100 will depend upon the type of sensor being utilized.

Referring now to FIGS. 2A-2D, shown therein is a pedometer 100 according to one embodiment of the present disclosure. As shown in FIG. 2A, the pedometer 100 is disposed external to the acetabular cup 32. In the illustrated embodiment, pedometer 100 has a first portion—adjacent to the acetabular cup—and a second portion—extending into the bone 10 adjacent to the acetabular cup 32. FIG. 2B shows the pedometer 100 in more detail. The pedometer 100 includes a main body 110. A head 112 of the pedometer 100 includes a flange portion 118. The leading end 114 of the pedometer 100 is adapted for being disposed within bone. To facilitate bone engagement the pedometer 100 includes threads 116. The threads 116 are configured such that the pedometer 100 may act as a bone screw. Thus, threads 116 should be of an appropriate size and shape to encourage bone engagement.

Figure 2D:
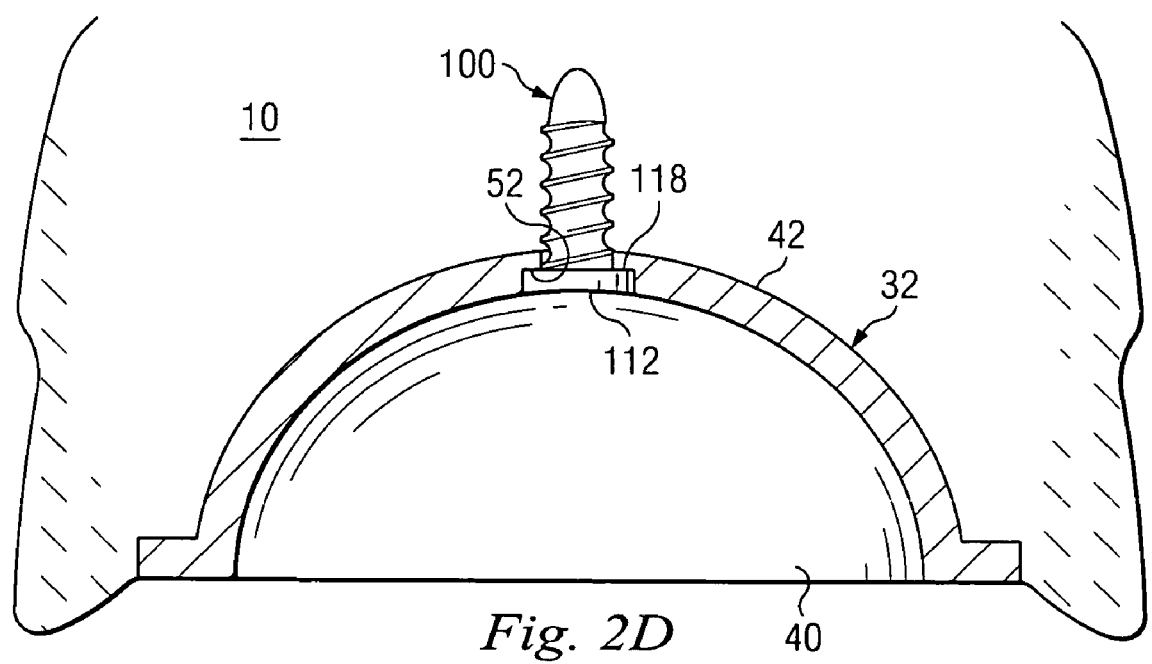
FIG. 2D is an enlarged cross-sectional side view of the implantable pedometer engaging the engagement area of the hip prosthesis and an adjacent bone.

As shown in FIG. 2C, the flange portion 118 is adapted for engaging internal flange 52 of opening 50 of the acetabular cup 32. The inner surface 40 of the acetabular cup 32 is adapted for movable engagement with the femoral head 34 of the hip implant 30. Flange portion 52 is recessed with respect to inner surface 40 of the acetabular cup 32 so that when flange portion 118 is engaged with flange 52 the head 112 substantially aligns with internal surface 40 and does not inhibit the movable engagement between the femoral head 34 and the inner surface 40. FIG. 2D shows pedometer 100 engaged with the bone 10 and the acetabular cup 32. An external surface 42 of the acetabular cup 32 also engages the bone 10. In the illustrated embodiment, it is also contemplated that the pedometer 100 may be implanted after the acetabular cup 32 has been implanted in a later surgical procedure. It is also contemplated that the pedometer 100 may be implanted when the acetabular cup 32 is implanted. It is also contemplated that the pedometer 100 may be implanted into a bone without engaging a portion of a previously implanted implant. That is, the pedometer 100 may be a stand-alone unit.

Figure 3:
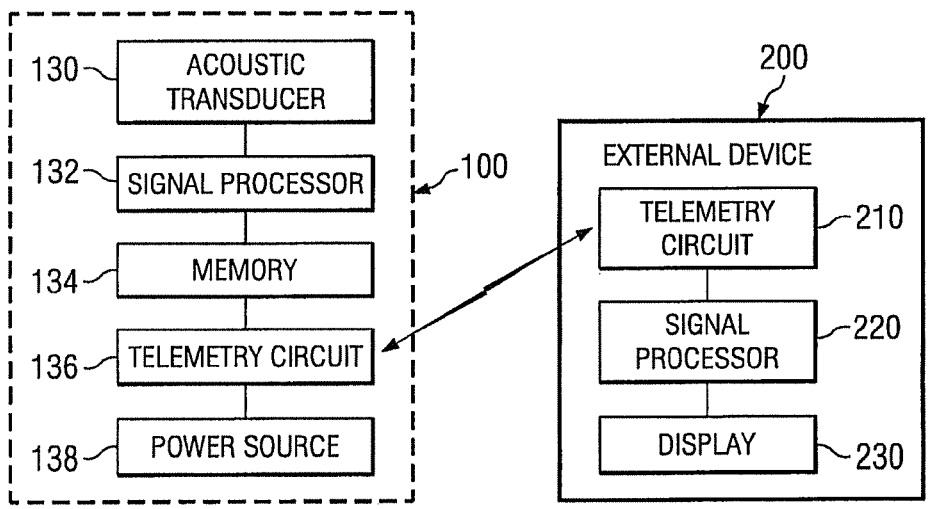
FIG. 3 is a schematic illustration of the implantable pedometer and external receiver of FIG. 1, where the implantable pedometer is in wireless communication with the external receiver.

FIG. 3 is a schematic illustration of the implantable pedometer 100 in wireless communication with an external receiver 200. The implantable pedometer 100 includes a sensor 130, a signal processor 132, a counter 134, a telemetry circuit 140, and a power supply 150. While the implantable pedometer 100 is described as having a separate signal processor 120, it is fully contemplated that the function of the signal processor, described below, may be incorporated into either the sensor or the counter 130, eliminating the need for a separate signal processor. Similarly, it is fully contemplated that the functions of the various components of the pedometer 100 may be combined into a single component or distributed among a plurality of components. Further, it is fully contemplated that the pedometer 100 may include other electronics and components adapted for monitoring implant usage.

In general, the implantable pedometer 100 functions by counting the number of signals detected that are indicative of use of the joint and then storing that count data for later retrieval by an external device 200. The type of signal detected is dependent upon the type of sensor 130 utilized in the pedometer 100. It is contemplated that the implantable pedometer 100 may use a variety of sensors including, but not limited to those adapted for detecting implant use from acoustic waves, vibrations, loads, impedance, and motion/movement. For example, each step taken by the patient evokes a sound that can be detected by an acoustic sensor. Similarly, each step also causes vibrations that can detected. Further, each step taken by the patient puts a load on the implant that can be detected by a load sensor or strain gauge. Finally, stepping, swaying, and other movements by the patient create motion that may be detected by an accelerometer or gyroscope.

In the currently described embodiment, the sensor 130 is an acoustic sensor. Thus, the sensor 130 is configured for detecting sounds and acoustic waves indicative of using the hip implant 30 such as walking. It is fully contemplated that the acoustic sensor may be an accelerometer. An accelerometer can be utilized to detect vibrations. In relation to acoustic sounds and waves detected, it is contemplated that the vibrations detected by an accelerometer may be a result of the acoustic emissions, the producing cause of the acoustic emissions, or the acoustic emissions themselves. Each time the sensor 130 detects a sound or wave indicating use of the hip implant 30, it sends a signal to the signal processor 132. If the signal meets the minimum threshold parameters, then the signal processor 132 will pass on the signal to the counter 134 to be counted. In this regard, the signal processor 132 may be utilized to set parameters or threshold levels of detection for the sensor 130. The signal processor 132 may set parameters such as the amplitude, frequency range, or decibel level required before a signal is counted. These parameters are to be set so as to increase the accurate measurement of implant usage. For example, setting the detection level criteria too low may cause inappropriate increases in implant usage where the implant has in fact not been used. On the other hand, setting the detection levels too high may cause the pedometer 100 to miss signals of implant use. This threshold determination performed by the signal processor 132 may be accomplished without the need of a separate signal processor by simply choosing or programming the sensor 130 or counter 134 to take such threshold parameters into account. It is contemplated that the patient may be instructed through a series of movements such as walking, climbing stairs, or cycling with the sensor detecting the associated indicators of movement. Then based on the sensed signals, the sensor threshold(s) may be set for initial operation.

The counter 134 is configured to keep a running count of the number of signals it receives from the signal processor 132. It is fully contemplated that the counter 134 may utilize a scaling function to save on memory and size requirements. For example, the counter may be scaled such that each 1,000 signals received corresponds to a single count. On the other hand, it is also contemplated that the counter 134 may store additional data with respect to each signal such as a timestamp, the specific characteristics of the signal, or any other relevant data. In this light, the counter 134 may be configured to keep the types of data the orthopedic surgeon or treating physician would like to have to monitor implant usage.

The implantable pedometer 100 also includes a telemetry circuit 136. The telemetry circuit 136 is connected to the counter 134 and is adapted for sending the count data stored in the counter outside of the patient's body to an external receiver 200. In particular, the telemetry circuit 136 is adapted for communicating wirelessly with the telemetry circuit 210 of the external receiver 200. There are several types of wireless telemetry circuits that may be employed for communication between the implantable pedometer 100 and the external receiver 200. For example, RFID, inductive telemetry, acoustic energy, near infrared energy, "Bluetooth," and computer networks are all possible means of wireless communication. In the present embodiment, the telemetry circuits 136, 210 are adapted for RFID communication such that the telemetry circuit 136 is a passive RFID tag. Using a passive RFID tag helps limit the power requirements of the telemetry circuit 136 and, therefore, the implantable pedometer 100 yet still allows wireless communication to the external receiver 200.

Supplying the power requirements of the implantable pedometer 100 is a power source 138. In the current embodiment, the power source 138 is a battery. The battery used as a power source 138 may be a lithium iodine battery similar to those used for other medical implant devices such as pacemakers. However, the battery power source 138 may be any type of battery suitable for implantation. Further, the battery may be rechargeable. For example, the battery may be configured such that an externally applied electromagnetic field will recharge the battery. A rechargeable battery of this type would extend the life of the pedometer without requiring a surgical procedure to replace the battery. It is also contemplated that the power source 138 may a capacitor or array of capacitors. Using a capacitor provides an alternative form of replenishable power source to the rechargeable battery.

The power source 138 is connected to one or more of the sensor 130, the signal processor 132, the counter 134, or the telemetry unit 136. The battery power source 138 is connected to these components so as to allow continuous monitoring of implant usage. The sensor 130 may use the power source 138 to facilitate the sending of signals to the signal processor 132. The signal processor 132, in turn, may use the power source 138 to accomplish its processing and then to send a signal count to the counter 134. The counter 134 will then use the power source 138 to increment the count data and store the data.

In other embodiments the power source 138 may also be connected to the telemetry circuit 136 to provide power to facilitate communication with the external receiver 200. However, in the present embodiment the telemetry circuit 136 does not require power from the power source 138 because it communicates with the external receiver 200 utilizing a passive RFID tag. Further, the power source 138 may be connected to other electronic components not found in the current embodiment. It is also fully contemplated that the power source 138 may include a plurality of batteries or other types of power sources. Finally, it is also contemplated that the implantable pedometer 100 may be self-powered, not requiring a separate power supply. For example, a piezoelectric transducer may be utilized as the sensor 130 such that piezoelectric transducer detects the use signal and converts it into an electrical signal sufficient to increment the count data. Then, as in the current embodiment, the pedometer may utilize a passive RFID tag or other passive telemetry unit to communicate the count data with an external device. Thus, allowing the pedometer 100 to function without a dedicated power source.

The external receiver 200 receives the count data from the implantable pedometer 100 via communication between the telemetry circuit 136 of the pedometer 100 and telemetry unit 210 of the external device 200. Then a signal processor 220 converts or demodulates the data. The converted data is output to a display 230 where it is displayed in human intelligible form. The conversion and processing of the data may be tailored to the specific liking of the surgeon. For example, the display of data may simply be a number representing the number of signals recorded by the counter 134. Similarly, the display of data may be a bar graph having a height or length representing the corresponding amount of implant usage. Further, the display may show a comparison of the patient's implant use with that of an accepted or established value for an average patient's use. These various display examples are for illustration purposes only and in no way limit the plurality of ways in which the count data may be displayed in accordance with the present invention.

Figure 4:
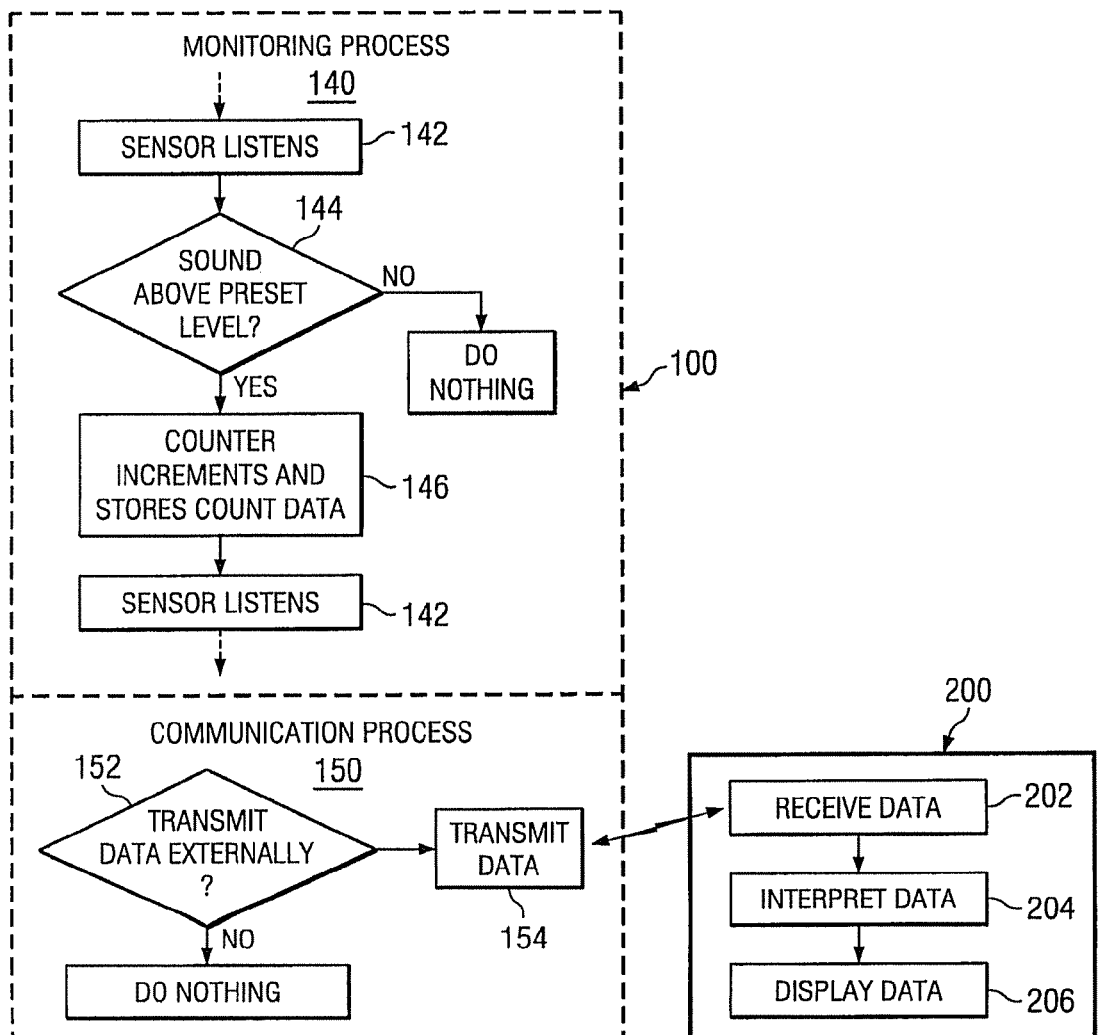
FIG. 4 is a flow chart illustrating use of the implantable pedometer and external receiver of FIG. 1.

FIG. 4 illustrates a possible flow chart for implant use data detection, processing, and output employing the current embodiment of the invention. The internal monitoring process 140 occurring within the pedometer 100 constitutes a continuous loop of monitoring and storing the amount of use of the hip implant 30. At step 142 the acoustic sensor 130 listens for signals indicative of implant usage. Upon detecting a signal, at step 144 the signal processor 132 determines if the signal meets the preset parameters. If the signal does not meet the minimum parameters, then the signal processor 132 does nothing. If the signal does meet the preset parameters, then the signal processor 132 passes along a count to the counter 134. At step 146, the counter 134 increments and stores the count data accordingly. The internal process continues as the acoustic sensor 130 listens for the next signal of usage at step 142.

Also within the pedometer, a communication process 150 is underway. At step 152, the telemetry unit 136 awaits communication from the external receiver 200 requesting transmission of the usage data. If the telemetry unit 136 receives such a request, then the telemetry unit 140 transmits the usage data to the telemetry unit 210 of the external receiver 200 at step 154. The external receiver 200 receives the usage data at step 202. From there, at step 204 the signal processor 220 converts or demodulates the transferred data and at step 206 the display 230 displays the demodulated data in human intelligible form. At this point the surgeon or caretaker can review the usage data and take the appropriate medical action as they see fit.

Though not illustrated, it is also contemplated that the external receiver 200 may reset the usage data stored within the pedometer 100. For example, the external receiver 200 may be configured to reset the count data to zero upon extraction of the usage data. The external receiver 200 may clear the memory of the pedometer 100 by utilizing communication between the telemetry circuits 140, 210. However, it is not necessary for the external receiver to clear the data of the pedometer 100. For example, a treating physician may wish to keep a running count of total implant usage rather than resetting the counter 134 after each data extraction.

Figure 5A:
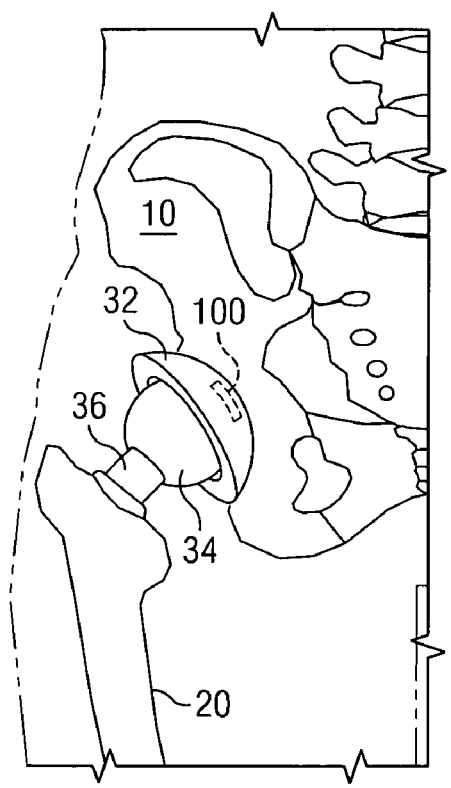
FIG. 5A is a front view of an implantable pedometer located within a hip prostheses according to one embodiment of the present invention.
Figure 5B:
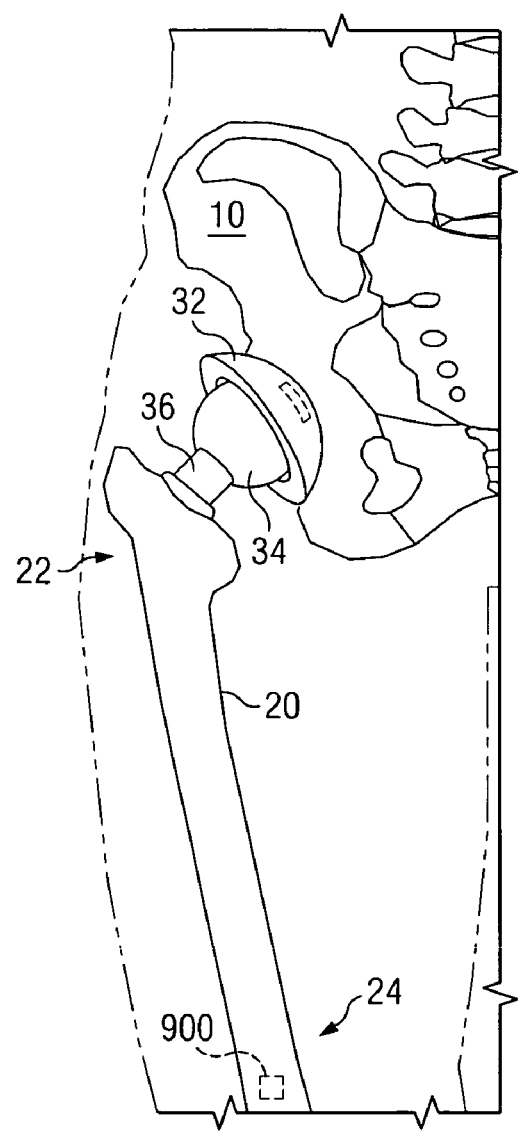
FIG. 5B is a front view of an implantable pedometer located distal to a hip prostheses according to one embodiment of the present invention.

Referring now to FIGS. 5A-5B, shown therein are various dispositions of a pedometer in accordance with the present invention. FIG. 5A shows the pedometer 100 disposed within the acetabular cup 32 of the hip implant 30. It is fully contemplated that the pedometer 100 may also be disposed within the femoral head 34 or stem 36 of the hip implant 30. Further, it is contemplated that the pedometer 100 may be disposed within a portion of the hip implant 30 during manufacture of the hip implant. However, where the pedometer 100 is to be disposed within a portion of the hip implant 30, it is preferred that the pedometer 100 be adapted for placement within one of the portions of the hip implant 32, 34, 36 after manufacture of the hip implant. For example, the pedometer 100 may be placed into an available opening of the implant or manually placed into a surface of the implant. In this manner the pedometer 100 may be utilized with the hip implant 30 regardless of the manufacturer of the hip implant.

FIG. 5B shows a pedometer 900 disposed in a position distal to the hip implant 30. Pedometer 900 may be substantially similar to pedometer 100. While the pedometer 900 is shown as being located on the lower or distal portion 24 of the femur 20, this is only one example of a distal location for the pedometer. Further, pedometer 900 may be used alone or in combination with another sensor located on the acetabular cup as shown in FIG. 5B. The exact distal locations available for disposition of the pedometer 900 will depend on the type of sensing technology used in the pedometer and the data sought by the medical professional. For example, a pedometer employing an acoustic sensor must be within range to detect the sounds or vibrations associated with patient movement and likely use of the implant. This range may vary depending on such factors as the sensitivity of the sensor, ambient noise or interference present in the patient, or the type and accuracy of data being sought.

Figure 6A:
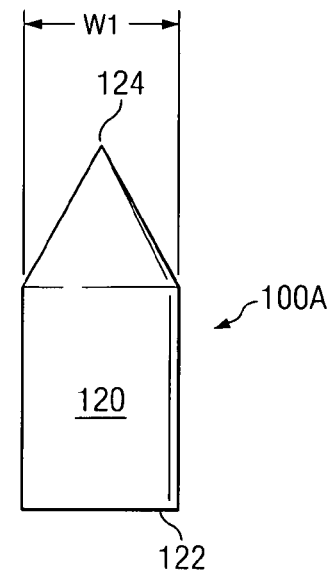
FIG. 6A is an enlarged view of an implantable pedometer according to one embodiment of the present invention.
Figure 6B:
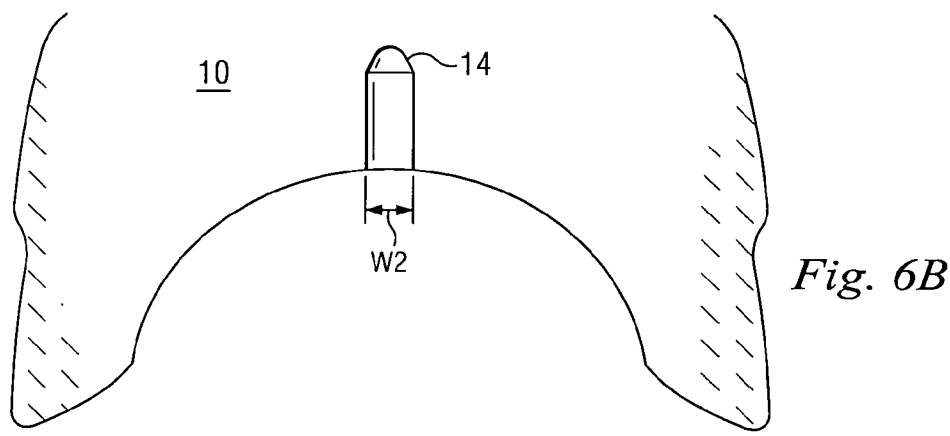
FIG. 6B is an enlarged cross-sectional side view of a portion of a prepared bone.
Figure 6C:
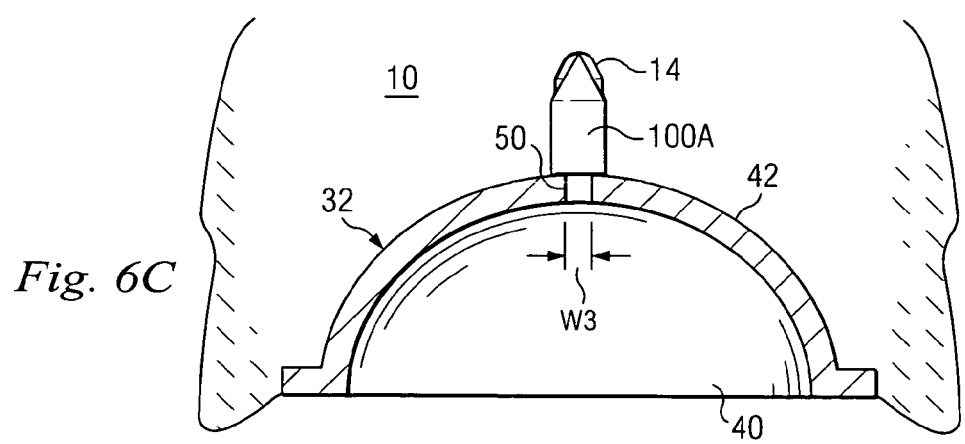
FIG. 6C is a cross-sectional side view of the implantable pedometer of FIG. 6A implanted within the prepared bone of FIG. 6B and a portion of hip prosthesis engaged with the bone of FIG. 6B.

FIGS. 6A-6C show a pedometer 100A adapted for being disposed at least partially within a bone 10. The pedometer 100A may be substantially similar to pedometer 100. The pedometer 100A includes a main body 120 having a width W1, an implant engagement portion 122, and a bone engagement portion 124. In the illustrated embodiment, the bone engagement portion 124 is substantially similar to a bone nail. However, bone engagement portion 124 and the pedometer 100A may be of any shape or form adapted for placement within a portion of a bone 10. In one embodiment, the pedometer 100A is substantially shaped like a coin and adapted for placement within a portion of bone.

FIG. 6B shows a prepared opening 14 in the bone 10. The prepared opening 14 has a width W2 that is slightly smaller than width W1 of the pedometer 100A. The prepared opening 14 and its width W2 are configured such that the pedometer 100A may be press-fit into the bone 10. It is contemplated that after the pedometer 100A has been press-fit into the prepared opening 14 that it may then be sealed into the bone. The pedometer 100A may be sealed into the bone using a variety of techniques. These sealing techniques may include, but are not limited to, fibrin glue, PMMA, collagen, hydroxyappetite, bi-phasic calcium, resorbable polymers or other materials suitable for implantation. Additionally or alternatively, the pedometer 100A may be sealed into the bone by a later implanted implant, or any combination of these techniques. For example, the pedometer 100A may be sealed in by any of the above mentioned materials in combination with an additional implant to provide enhanced fixation. In this manner, the pedometer 100A may be implanted either prior to the implantation of an implant or as a stand alone unit—where no implant is to follow.

FIG. 6C shows the pedometer 100A press-fit into the prepared opening 14 of the bone 10. Also shown is an implanted acetabular cup 32 having an inner surface 40, an external surface 42, and a driver opening 50. The external surface 42 of the acetabular cup 32 engages the bone 10. Driver opening 50 has a width W3 that is smaller than width W2 of the prepared opening 14 and, therefore, smaller than the width W1 of the pedometer 100A. In this manner the acetabular cup 32 may be used to seal the pedometer 100A into the bone. If the pedometer 100A was to come loose from the prepared opening 14 it would still not be dislodged as the acetabular cup would keep it in place. It is not necessary for driver opening 50 to seal the pedometer 100A into place, other portions of the acetabular cup 32 may be used.

In the illustrated embodiment, it is contemplated that the pedometer 100A may be implanted after the acetabular cup 32 has been implanted. Under one approach, the pedometer 100A may be impacted or otherwise advanced into the adjacent bone 10 until the threads of the implant engagement portion are in a position to be threaded into the threaded portion. Then the pedometer 100A may be rotated until the threads and threaded driver portion are fully threaded together. In another approach, the pedometer 100A may be driven into a bone without engaging an implant. Under such approach, the pedometer 100A functions as a stand-alone unit.

Figure 7:
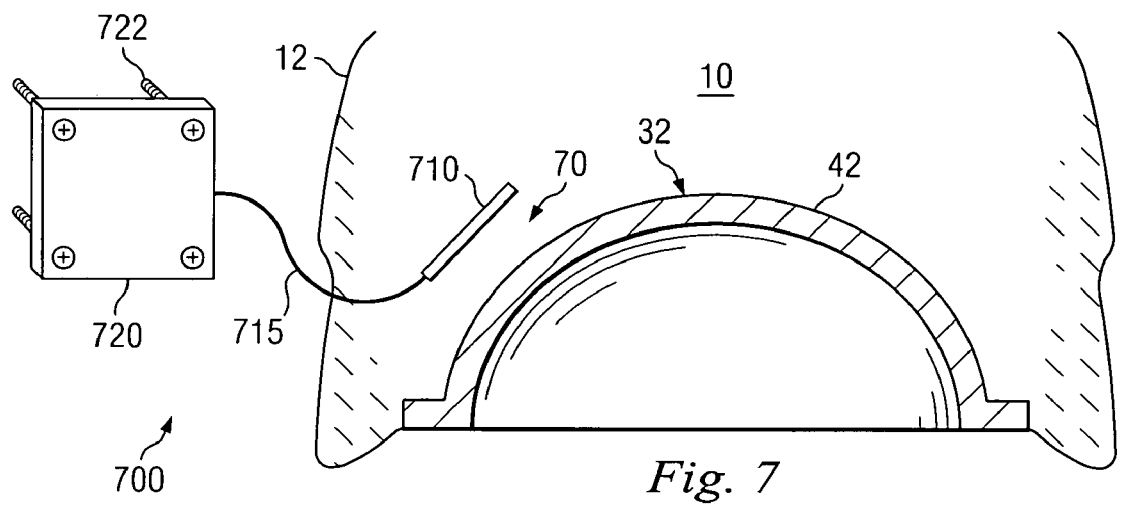
FIG. 7 is a cross-sectional view of a two-part implantable pedometer according to one embodiment of the present invention shown spaced apart from a portion of a hip prosthesis.

Referring now to FIG. 7, shown therein is an alternative embodiment of a pedometer for monitoring use of an implant in accordance with another aspect of the present invention. A pedometer system 700 is shown in a position for monitoring the use a hip joint. The pedometer 700 may be substantially similar to other pedometers described in accordance with the present invention. However, pedometer system 700 includes a sensor 710 for insertion into a bone and a main housing 720. It is contemplated that the main housing 720 will contain the remaining components of the pedometer system 700 such as a signal processor, counter, memory unit, telemetry unit, power supply, or any other component. As illustrated, the main housing 720 is adapted to be positioned away from the sensor 710. Main housing 720 is located outside of the exterior bone surface 12 of bone 10. Main housing 720 may be attached to the bone 10 via anchoring elements 722, that may be such things as spikes or screws. Main housing 720 may also be adapted for positioning within soft tissue. Positioning the main housing 720 away from the sensor 710 allows the sensor, which may be miniaturized, to be placed in a desired location without requiring the additional space to house the remaining components of the pedometer system 700.

Figure 11A:
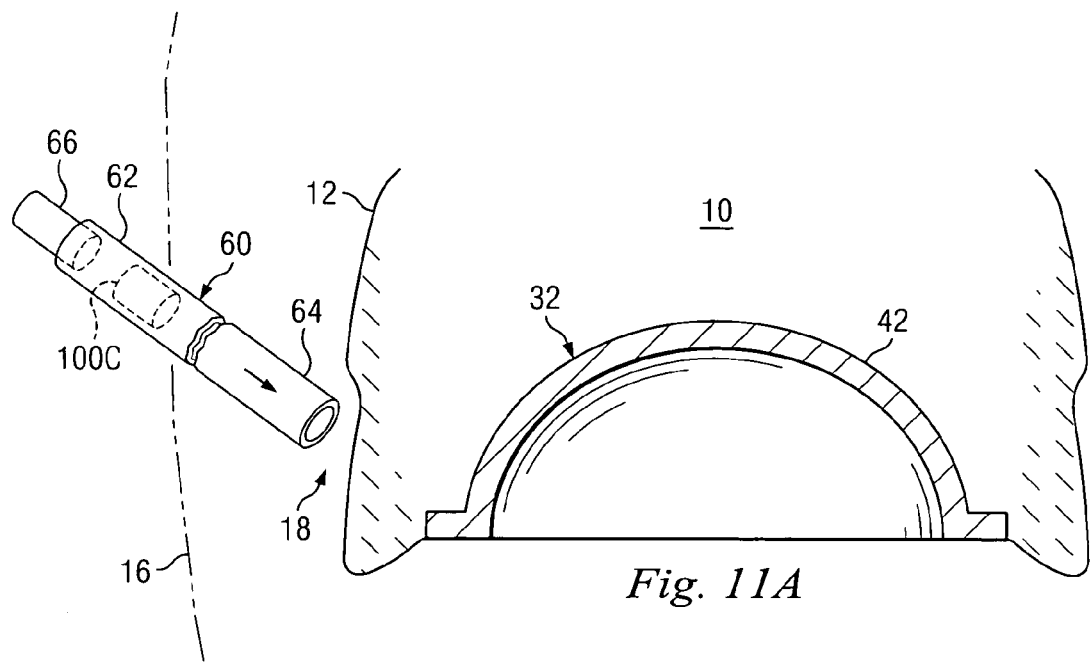
FIG. 11A is a cross-sectional view of an implantable sensor according to one embodiment of the present invention being implanted via a cannula.

The Sensor 710 may be substantially cylindrical or any other shape configured to be delivered to the implantation site via a catheter or needle. It is contemplated that the sensor 710 may take the shape of a coin or similar object. It is also contemplated that the sensor 710 may be an elongated cylinder. For example, in one embodiment of the elongated cylinder sensor the length is at least three times the diameter of the cylinder. Similarly, the main housing 720 may be adapted and shaped so as to allow implantation via a catheter. Further, in embodiments of the present invention where the pedometer is a single unit, the entire pedometer may be adapted for insertion via a catheter as shown in FIG. 11A.

In the currently illustrated embodiment, since the sensor 710 will be disposed away from the main housing 720 it must be configured to communicate with the components of the main housing. In this respect, the sensor 710 may communicate with the components in the main housing 720 via a dedicated wire 715 as shown. On the other hand, the sensor 710 may communicate with the components in the main housing 720 wirelessly. For example, the sensor 710 may utilize an RF transponder or other means of wireless communication to transfer information to the main housing 720.

Though the main housing 720 is shown as being disposed near the hip joint, it is fully contemplated that the main housing may be disposed anywhere within communication range of the sensor 710. Thus, the main housing 720 is preferably located where it will not interfere with use of the joint nor interfere with any other body functions. Where the sensor 710 communicates with the components of the main housing 720 via the wire 715, the location of the main housing is limited by potential interference of both the wire and the main housing. Where the sensor 710 communicates with the components in the main housing 720 wirelessly, the position of the main housing 720 will be a function of the limits on the distance for wireless communication as well as any potential body function interference the main housing may cause. With sufficient wireless communication or placement of the sensor 710 near the surface of the body, it may be possible to position the main housing 720 externally. That is, the main housing 720 may be positioned outside the patient's body. Preferably, when disposed outside of the body the main housing 720 will be positioned in a location anatomically close to the sensor 710. Placing the main housing 720 as close to the location of the sensor 710 as possible helps to facilitate wireless communication. It is not necessary to place the main housing 720 near the sensor 710 if communication can be achieved from greater distances.

FIG. 7 shows the sensor 710 implanted within bone 10 near an acetabular cup 32 but spaced apart from the acetabular cup as illustrated by gap 70. Gap 70 is shown relatively large for the purposes of illustration. However, gap 70 may be much smaller than the thickness of the sensor or the implant. In the illustrated embodiment, it is contemplated that the pedometer system 700 may be implanted percutaneously either prior to or after implantation of the acetabular cup. The size and shape of the components of the pedometer system 700 may be adapted for insertion through a catheter or any other percutaneous means of insertion. For example, it is contemplated that the sensor 710 be miniaturized to facilitate ease of placement in any desired location. Implanting the pedometer system 700 may be a minimally invasive procedure. In this manner, the pedometer system 700 may be utilized to monitor the use of a joint prior to the need for artificial joint replacement surgery without causing severe trauma to the patient or furthering injuring the joint to be monitored. Similarly, the pedometer system 700 may be implanted after joint replacement surgery without requiring open surgery or otherwise compromising the integration of the implant into the body.

Figure 8A:
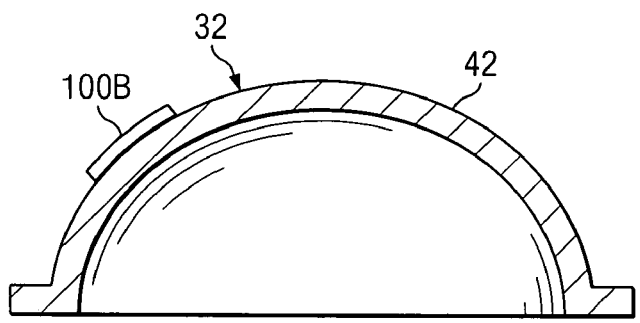
FIG. 8A is a cross-sectional view of an implantable pedometer according to one embodiment of the present invention attached to a portion of an exterior surface of a hip prosthesis.
Figure 8B:
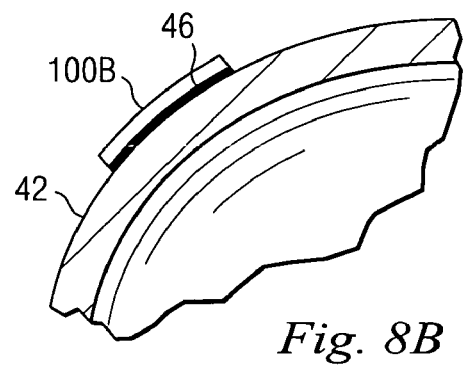
FIG. 8B is an enlarged cross-sectional view of the implantable pedometer and exterior surface shown in FIG. 8A.

Referring now to FIGS. 8A-8B, shown therein is an alternative embodiment of a pedometer for monitoring use of a joint in accordance with another aspect of the present invention. FIGS. 8A and 8B show an implantable pedometer 100B attached to a surface 42 of an acetabular cup 32 and adapted for monitoring indicators of joint use. It is contemplated that the pedometer 100B may be associated with surface 42 without being fixedly mounted. However, it is also contemplated that the pedometer 100B may be attached to the surface 42 of the acetabular cup 32 by any reliable means. One means of attachment is fibrin glue. Fibrin glue may be utilized to secure the pedometer 100B to the surface 42. As shown in FIG. 8B, a very thin interface layer 46 of fibrin glue may be sufficient to glue the pedometer 100B to the implant. It is contemplated that the pedometer may be attached to the implant prior to implanting the implant. However, it is also contemplated that the pedometer be attached to the implant at some time after implantation.

Referring now to FIGS. 9A-9D, shown therein are alternative embodiments the implantable pedometer in accordance with the present invention. These alternative embodiments illustrate the various combinations of electronic and non-electronic components that may be utilized by the pedometer to monitor implant usage. These illustrations are exemplary of the type of combinations that may be employed by the pedometer, but in no way are these illustrations intended to limit the types of electronic and non-electronic components or combinations thereof that may be utilized in accordance with the present invention.

Figure 9A:
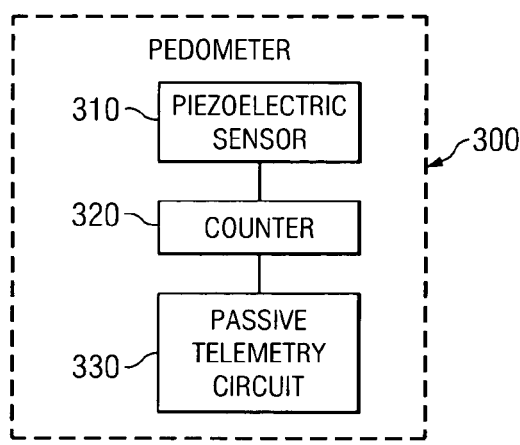
FIG. 9A is a schematic illustration of an implantable pedometer according to one embodiment of the present invention.

FIG. 9A shows a pedometer 300 having a piezoelectric sensor 310, a counter 320, and a passive telemetry unit 330. The pedometer 300 is an example of a pedometer in accordance with the present invention that does not require a dedicated power source. The pedometer 300 utilizes the piezoelectric sensor to generate the energy or voltage necessary to increment the counter 320. The data stored by the counter 320 is transferred to an external device (not shown) via the passive telemetry unit 330. The passive telemetry unit 330 may utilize one of a variety of passive communication methods. For example, the passive telemetry unit 330 may utilize inductive or capacitive coupling from the external device to facilitate communication. If inductive coupling is used, then the passive telemetry unit 330 may include a coil and/or an antenna to assist in the transfer of energy and data between the passive telemetry unit and the external device.

Figure 9B:
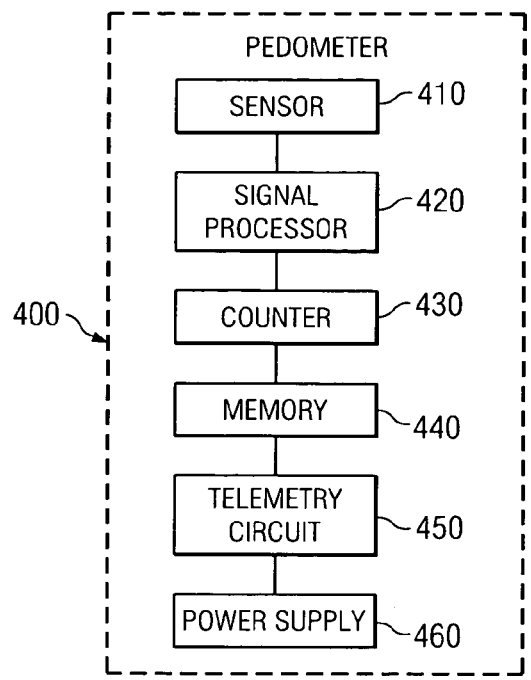
FIG. 9B is a schematic illustration of an implantable pedometer according to one embodiment of the present invention.

FIG. 9B shows a pedometer 400 having a sensor 410, a signal processor 420, a counter 430, a memory unit 440, a telemetry unit 450, and a power supply 460. Pedometer 400 may be substantially similar to other embodiments of the present invention, however, pedometer 400 includes a separate memory unit 440. While it is fully contemplated that the pedometer 400 may incorporate the function of the memory unit 440—storing data—into another component, such as the counter 430, having a separate memory unit may be particularly advantageous. For example, as memory units become increasingly smaller and cheaper while simultaneously increasing in capacity it may be possible to increase the available memory of the pedometer 400 without having to replace other components. Further, it is contemplated that the pedometer 400 may be able to observe and store more data than simply count usage. For example, by utilizing an accelerometer or gyroscope for the sensor 410 to measure implant usage the type of motion detected may be indicative of a certain type of movement such as walking, running, swaying side-to-side, riding a bicycle, or swimming. Similarly, various types of movements may produce a certain acoustic noise or vibration that can be distinguished by an acoustic sensor and sorted accordingly. In continuation, each of these various types of movements causes a different amount of wear on the hip implant. Thus, it may be advantageous to utilize a dedicated memory unit 440 to store the data in groups based on the amount of wear each movement creates. Note, use of a hip implant is for example only. This grouping function may be utilized with all types of implants where various types of actions may cause a different amount of wear to the implant. In this manner a more accurate representation of implant usage may be obtained and stored.

Figure 9C:
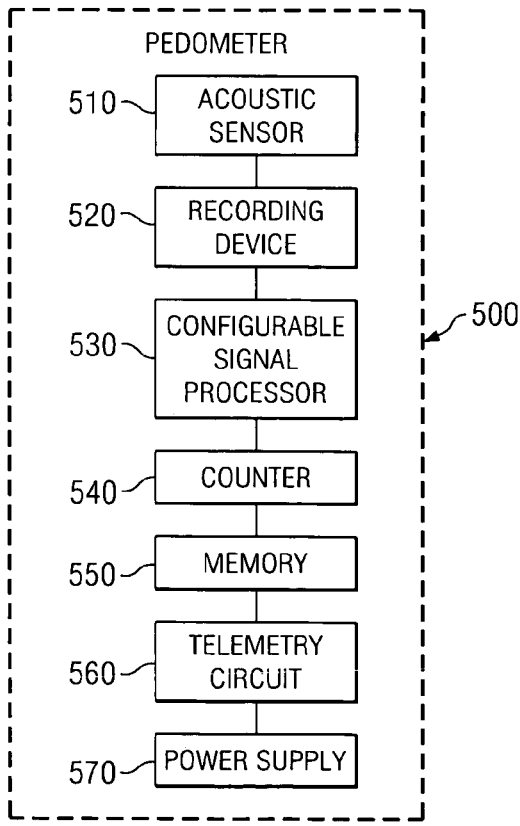
FIG. 9C is a schematic illustration of an implantable pedometer according to one embodiment of the present invention.

FIG. 9C shows a pedometer 500 having an acoustic sensor 510, a recording device 520, a configurable signal processor 530, a counter 540, memory unit 550, a telemetry unit 560, and a power supply 570. Pedometer 500 may be substantially similar to other embodiments of the present invention, however, as illustrated pedometer 500 includes a recording device 520 and a configurable signal processor 530. In regard to the recording device 520, it is known that there are certain sounds indicative of patient activity. Specifically the pounding of walking and running may be sensed and recorded as an indicator of joint usage. Additionally, but not required, other sounds indicative of implant degradation may be detected. The pending patent application Ser. No. 11/344,667 entitled "Implantable Sensor," filed on even date is incorporated herein by reference in its entirety. For example, associated with the wear of a hip implant are sounds of "play" or movement within the components of the hip implant itself or between the hip implant and the surrounding bone. This play may be characterized by a clicking sound caused by the worn hip implant socket. Similarly, with the onset of osteolytic lesions the bone begins to create "mushy" or "soft" sounds with each step taken. As indicated above, osteolytic lesions are often caused by polyethylene wear debris from deteriorating implants. In this manner, the pedometer 500 may be utilized for the detection of osteolytic lesions as well as for monitoring implant use. Thus, it is advantageous for the pedometer 500 to include a means of detecting and recording these sounds for later review by a surgeon or other caretaker.

It is contemplated that acoustic sensor 510 may be a microphone or other type of sensor that facilitates detection and recording of sounds indicative of implant deterioration. The acoustic sensor 510 is connected to the recording device 520 such that the recording device is able to store the sounds picked up by the sensor. However, due to a desire to minimize the size of the pedometer 500 so as to be minimally invasive, it may not be practical to record all of the sounds picked up by the sensor. Therefore, the recording device 520 may include a buffer—such as a 5-30 second buffer—allowing the pedometer 500 to review the sounds and only store those sounds meeting a predetermined criteria. It is contemplated that this determination will be made by the configurable signal processor 530. For example, the configurable signal processor 530 will monitor the sounds collected by the recording device 520 for the predetermined criteria. If a sound meets the criteria then that recording will be moved from the buffer and stored in the memory unit 550 for later retrieval by an external unit. If a sound does not meet the criteria, then it will simply be ignored and the recording process will continue.

Recordings stored in the memory unit 550 may later be removed by an external device. As with other embodiments, it is contemplated that the external device will communicate with the pedometer 500 via the telemetry unit 560. Once the external device has obtained the recordings from the memory unit 550 via the telemetry unit 560, then the recordings may either be played by the external device itself or transferred to another external unit adapted for playing the recordings such as a speaker or other sound producing unit. In this manner the patient's doctor or a specialist may review the recorded sounds for indications of wearing of the implant or the onset of osteolytic lesions and choose a treatment plan accordingly. Similarly, the recordings may be analyzed using spectral analysis. Spectral analysis may include such analyzing techniques as Fast Fourier Transform algorithms, fuzzy logic, artificial intelligence, or any other method of analyzing the data. Utilizing spectral analysis may identify patterns in the sounds or detect problems that a general doctor or even a specialist might miss in reviewing the recordings. On the other hand, spectral analysis may provide a vehicle for allowing the doctor or specialist to better identify problems by converting the data into various visual forms such as spectrograms or other graphical representations.

It is also contemplated that the sound recordings may be analyzed with respect to each other over time. The sound recordings do not have to be analyzed individually to establish implant usage. Rather, comparing sound recordings over the life of the implant may provide indications of implant degradation or the onset of osteolytic lesions. It is contemplated that the sound recordings will change as the implant is initially integrated, then fully integrated, and then begins to degrade. Thus, comparing sound recordings over intervals may provide insight into implant usage and the potential for osteolytic lesion development.

It is not necessary for the pedometer 500 to include a buffer. For example, the pedometer 500 may have a memory unit 550 adapted for storing a certain amount of recordings of the recording device 520 such as hours, days, weeks, or months worth of recordings or in terms of memory usage a certain number of bytes. Using such an approach, the data may be removed from memory unit 550 by an external device on an interval corresponding to the storage capacity of the memory unit. Thus, if the pedometer 500 is configured for storing 30 hours worth of recordings on the memory unit 550, then a daily synchronization with the external device that removes and stores the recordings may be appropriate. Also this approach may obviate the need for including the signal processor 530 within the pedometer 500. This is because, if all of the sounds observed by the sensor 510 are being recorded by the recording device 520, then the signal processing may be accomplished externally, either by the external device used to extract the data from the pedometer 500 or another device, such as a computer, that may obtain the data from the external device and perform the signal processing.

If the pedometer 500 does include a buffer and the signal processing is accomplished within the pedometer, then it may be advantageous to also include a configurable signal processor 530. The configurable signal processor 530 is utilized as described above to discriminate between sounds satisfying a predetermined criteria and those that do not. Additionally, the configurable signal processor 530 is adapted for keeping track of implant usage data as in other embodiments. That is, in addition to determining whether a certain recording should be kept the configurable signal processor 530 also determines when the counter should be incremented. Thus, the pedometer 500 may keep both implant usage data, including grouping by types of motions, as well as sound recordings for the caretaker to review in assessing the proper method of treatment for the patient.

The configurable signal processor 530 is also adapted for being configured by the external device. In this regard, the configurable signal processor 530 may communicate with the external device either via the telemetry circuit 560 of the pedometer 500 or through a separate communication path. Either way, the external device may set, restore, or change such aspects of the configurable signal processor 530 as the predetermined criteria for keeping sound recordings, the type of implant use data to be kept, the preset thresholds for incrementing the counter for tracking implant use, or any other setting related to the performance of the signal processor. Thus, a doctor can adjust the monitoring standards for the patient as conditions or available information changes. For example, as the amount of time the patient has had the implant increases the doctor may increase the sensitivity, amount, and types of data being stored. Similarly, as medical research develops in this area and more is known of the specific sounds or signals indicative of either different types of movements or implant wear, the pedometer 500 may be adjusted via the configurable signal processor 530 to take such things into account and store the desired data accordingly.

Figure 9D:
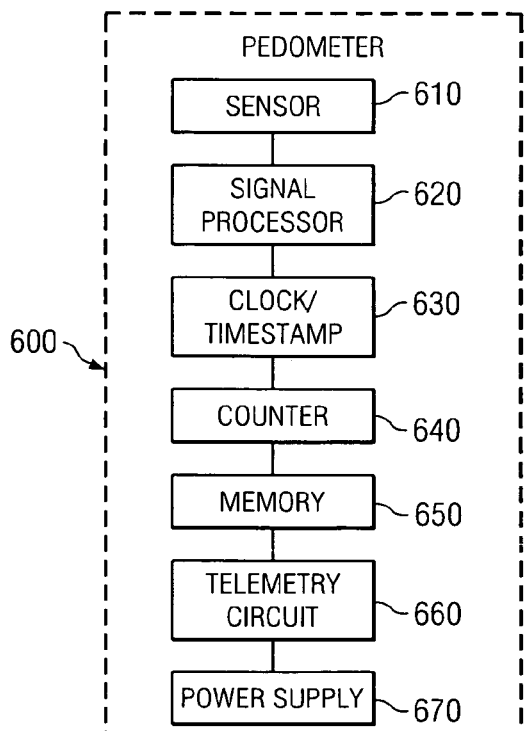
FIG. 9D is a schematic illustration of an implantable pedometer according to one embodiment of the present invention.

FIG. 9D shows a pedometer 600 having an acoustic sensor 610, a signal processor 620, a clock/timestamp 630, a counter 640, a memory unit 650, a telemetry unit 660, and a power supply 670. Pedometer 600 may be substantially similar to other embodiments of the present invention, however, pedometer 600 includes a clock/timestamp 630. While the clock/timestamp 630 is distinguished as a separate component of pedometer 600, it is fully contemplated that the clock/timestamp 630 may be integrated into another component of the pedometer such as the counter 640 or memory unit 650. The purpose of the clock/timestamp 630 is to provide time information along with the usage data. In this respect, each increment of the counter may be accompanied with a timestamp of the time of day. In this manner, a treating physician may then be able to review the patient's implant usage with respect to time and tailor a treatment plan accordingly. This may be particularly useful where the pedometer 600 utilizes a load or motion sensor or any other type of sensor that provides information regarding the extent of force or wear being applied to implant by a single movement. For example, if the implant use data indicates a significant amount of wear or force being applied to the implant between 8:00 a.m. and 9:00 a.m., the doctor may inquire into the activities of the patient during that time frame and either ask the patient to minimize or stop those activities or provide the patient with an alternative way of performing those activities that may put less strain and wear on the implant.

Described below are numerous alternative embodiments of the external receiver in accordance with the present invention. These alternative embodiments illustrate the various combinations of electronic and non-electronic components that may be utilized by the external receiver. These descriptions are exemplary of the type of combinations that may be employed by the external receiver, but in no way are these illustrations intended to limit the types or combinations of electronic and non-electronic components that may be utilized in accordance with the present invention.

In one embodiment the external receiver includes a telemetry unit, a signal processor, and an indicator. The external receiver may be substantially similar to other embodiments of the present invention. The telemetry unit is adapted for communication with an implantable pedometer in accordance with the present invention. Thus, the telemetry unit is configured to extract implant usage data from the pedometer.

As described previously, the telemetry unit may obtain data from the pedometer through a variety of wireless communication methods such as inductive coupling, capacitive coupling, radio frequency, personal computer networking, Bluetooth, or other wireless means. Though the preferred method of communication is wireless, it is also contemplated that the external receiver may be in selective wired communication with the implantable pedometer.

Once the data is obtained by the external receiver using the telemetry unit, the data is processed by the signal processor. The degree and type of data processing is dependant on both the data obtained from the implantable pedometer and the desires of the treating doctor. The data processing performed by the signal processor may range from simple conversion of count data into a human sensible form to complex analysis of the usage data via spectral analysis. Further, the data processing performed by the signal processor may only be a first step of processing. The processed data of the signal processor may be output to a more powerful or specialized signal processing unit (not shown) where additional processing takes place. This second signal processing unit may be located either in the external receiver itself or in a separate external device such as a personal computer.

The signal processor is adapted for converting the data into a form that may be utilized by an indicator. The indicator may be any type of device or interface that can output the data in human intelligible form. For example, the indicator may be a visual display. Where the indicator is a visual display it may display such things as a pure number representative of implant usage (e.g., increments of the counter), a color based on usage (e.g., green for minimal use, yellow for moderate use, and red for heavy use), a graph or chart representing usage, or any other visual display indicative of implant usage or other stored data. As another example, the indicator may be a speaker. Where the indicator is a speaker it could do such things as beep a certain number of times based on usage data (e.g., once for minimal use, twice for moderate use, or three times for heavy use), could audibly speak the number of increments counted, or produce any other audible message indicative of implant usage or other stored data. It is contemplated that the indicator may be composed of a plurality of output mechanisms instead of a single device.

In another embodiment the external receiver includes a telemetry unit, a calibration circuit, a signal processor, a memory unit, and a network interface. The external receiver may be substantially similar to other embodiments of the present invention. The external receiver includes a calibration circuit. The calibration circuit is adapted for configuring the configurable signal processor of an implantable pedometer. The external receiver may set, restore, or change such aspects of the configurable signal processor as the predetermined criteria for keeping sound recordings, the type of implant use data to be kept, the preset thresholds for incrementing the counter for tracking implant use, or any other setting related to the performance of the configurable signal processor. It is fully contemplated the calibration circuit may utilize the telemetry circuit to communicate with the configurable signal processing unit. However, it is also fully contemplated that the calibration circuit and the configurable signal processing unit may have a separate dedicated means of communication.

The external receiver also includes a memory unit. The memory unit may be adapted for multiple uses. First, the memory unit may be adapted for permanent storage of usage data obtained from an implantable pedometer in accordance with the present invention. Thus, the memory unit may store data obtained at various times from the implantable pedometer so the data may later be reviewed, compared, or analyzed. Second, the memory unit may be adapted for temporary storage of usage data obtained from the implantable pedometer. In this case, the memory unit will store the data until it is either discarded or transferred for permanent storage. For example, the data may be transferred from the memory unit via a networking interface to a network or computer for permanent storage.

The networking interface provides a means for the external receiver to communicate with other external devices. The type of network utilized may include such communication means as telephone networks, computer networks, or any other means of communicating data electronically. The networking interface of the external receiver could obviate the need for the patient to even go into the doctor's office for obtaining implant usage data. For example, the patient could utilize the external receiver to obtain the usage data from the implantable pedometer on a scheduled basis (e.g. daily, weekly, monthly, etc.). Then, utilizing the networking interface the patient could send this data to the treating doctor. The networking interface may be configured to directly access a communication network such as a telephone or computer network for transferring the data. It is fully contemplated that the computer network be accessible by a treating physician for reviewing implant usage data of the patient without requiring the patient to make an actual visit to the doctor's office. The networking interface may be similar to the CareLink system from Medtronic, Inc.

Further, it is also contemplated that any communication between the external receiver and the computer network may be encrypted or otherwise secured so as protect the patient's privacy. It is also contemplated that the networking interface may be configured for communication with a separate device that is adapted for accessing the communication network. For example, the networking interface may be a USB connection. The external receiver may be connected to a personal computer via the USB connection and then the personal computer may be utilized to connect to the communication network, such as the internet, for transferring the data to a designated place where the treating doctor may receive it.

Referring now to FIG. 5B, shown therein is an alternative embodiment of a system for monitoring use of an implant in accordance with another aspect of the present invention. The hip prostheses 30 being monitored includes an acetabular cup 32 configured for engagement with a prepared portion of the patient's acetabulum 10. The hip prostheses 30 also includes a femoral head 34 and a femoral stem 36. The femoral head 34 is configured for movable engagement with the acetabular cup 32 so as to create ball-in-socket motion. The femoral stem 36 is adapted for engaging a proximal portion 22 of the patient's femur 20. The ball-in-socket motion between the femoral head 34 and the acetabular cup 32 simulates the natural motion of the patient's hip joint.

Figure 10:
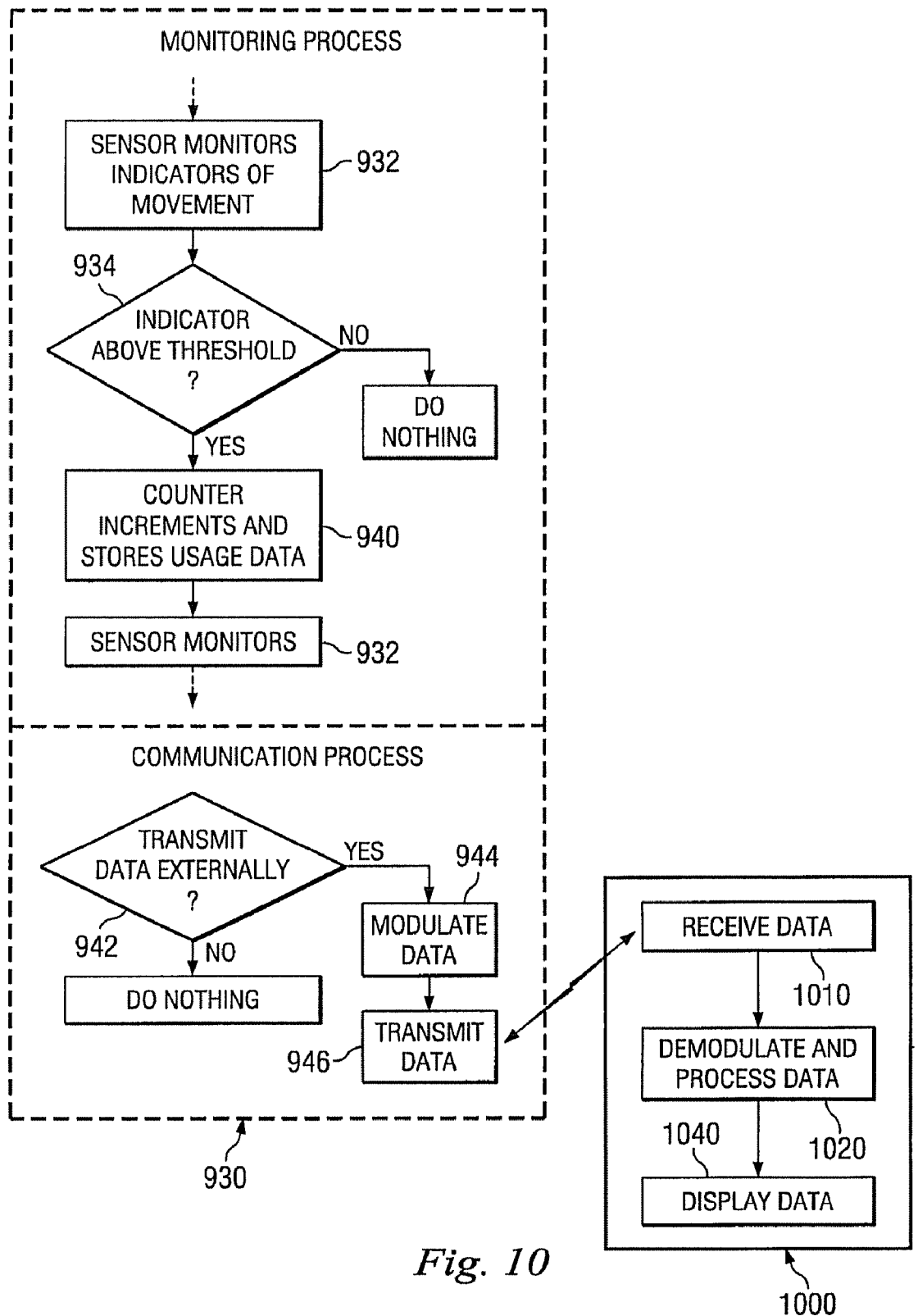
FIG. 10 is a flow chart illustrating use of the implantable pedometer and external receiver according to one embodiment of the present invention.

As shown in FIG. 5B, the implantable pedometer 900 is disposed within a proximal portion 22 of the patient's femur 20 and adjacent to the femoral stem 36 of the implant 30. The pedometer 900 may be positioned within the proximal portion 22 or the distal portion 24 of the femur 20. For example, the pedometer 900 may be positioned such that as the femoral stem 36 is inserted into the proximal portion 22 of the femur 20 the pedometer is forced into the bone structure by the femoral stem. On the other hand, the proximal portion 22 of the femur 20 may be prepared to receive the pedometer 900, the pedometer may be inserted, then the femoral stem 36 may be joined to the femur. In this manner, the pedometer 900 may be inserted in the original surgical procedure for inserting the implant. Note, however, that pedometer 900 may be positioned elsewhere. For example, the pedometer 900 may be positioned within or on the surface of the implant 30. Similarly the pedometer 900 may be positioned within or on the femur 20. The pedometer 900 is configured so that it may be positioned at any point where its sensor 910 may detect movements indicative of implant usage or wear. As such, it is fully contemplated that the pedometer 900 may be introduced after the original surgical procedure for inserting the implant into such a position As illustrated in FIG. 10, the implantable pedometer 930 includes a motion sensor, a signal processor, an amplifier, a counter, a modulator, a telemetry unit, and a power source. It is fully contemplated that the functions of each of these components, described below, may be performed by the other components or further distributed among additional components not shown. The motion sensor is adapted for detecting movements indicative of implant usage at step 932. For example, the motion sensor may detect such movements as stepping and swaying. In its simplest form the pedometer 930 may simply count the number of movements detected by the motion sensor and increment the counter accordingly in step 940. However, in a more advanced form the pedometer 900 and in particular the motion sensor 910 may be adapted for detecting and discriminating between various types of movements. Thus, the motion sensor 910 may distinguish between walking, running, swaying, turning, jumping, swimming, riding a bicycle, lifting, or any other characteristic movement. In this more advanced form the pedometer 900 may be adapted for storing usage data based on these various groupings of movements.

It is contemplated that motion sensor 910 may utilize accelerometers, gyroscopes, or a combination of both. Further, while motion sensor 910 is illustrated as a single component it is fully contemplated that the motion sensor 910 may be comprised of a plurality of individual sensors. In the case of a plurality of sensors, the sensors may either work together to aid in implant usage detection or may simply be redundancies to one another. The amount of data that may be obtained from the sensors will depend on the type of accelerometer or gyroscope used.

For example, depending on whether a single-axis, dual-axis, or three-axis accelerometer is utilized the available data will be very different. Where a single-axis accelerometer is used differentiating between various types of movements is very difficult. This is because different movements may have similar movements when viewed with respect to the single axis of measurement. On the other hand, using a three-axis accelerometer allows for an increased ability to differentiate between the various types of movements. Note that multiple single-axis accelerometers may be utilized to recreate the advantages of multiple-axis accelerometers. Similarly, the number of degrees of freedom utilized in a gyroscope will determine the amount and type of information that may be derived from the data. As with the accelerometer, the more degrees of freedom utilized the more information that will be available for the orthopedic surgeon or treating doctor to review. When looking to obtain the most amount of data the gyroscope would have six degrees of freedom. In other cases, the gyroscope would have fewer degrees of freedom, but preferably at least three degrees of freedom.

Once the motion sensor 910 detects an indicator of motion the sensor outputs a corresponding signal to the signal processor 920. The signal processor 920 and an amplifier 930 are utilized for signal processing. For example, the signal processor 920 and amplifier 930 may be used to determine whether the indicator detected is above a threshold. When the indicator of movement is above the threshold the processor 920 and amplifier 930 may be used to send signals to the counter 940 for incrementing the usage count. As in other embodiments, the counter 940 is utilized for counting the number of movements related to use of the implant and storing implant usage data. Second, the signal processor and amplifier 930 may be used to convert data into a storable form. For example, the signal processor 920 and amplifier 930 may utilize various types of data compression to minimize the amount of memory required or increase the amount of data that may be stored. Third, the signal processor 920 and the amplifier 930 may be used to sort the data or perform analysis of the data before storage. Finally, the signal processing performed by the signal processor 920 and the amplifier 930 may be tailored to the individual liking of an orthopedic surgeon or treating physician.

The pedometer 930 also includes a modulator. The modulator is adapted for converting the implant usage data into a transmittable form in step 944. Once modulated, the implant usage data may be sent via a telemetry unit in the transmittable form to an external device 1000 in step 946. It is fully contemplated that the modulation and transfer of the data may be performed entirely by the telemetry unit itself. Once the data has been transferred to the external device 1000, it is demodulated or converted by a demodulator in step 1020. Then the data is processed by signal processor into a form that may utilized by an indicator also in step 1020. Once again, it is fully contemplated that the demodulation and data processing may be entirely performed by a single unit. The indicator, in step 1040, then provides the data in a human intelligible form for review by the surgeon or caretaker.

Figure 11B:
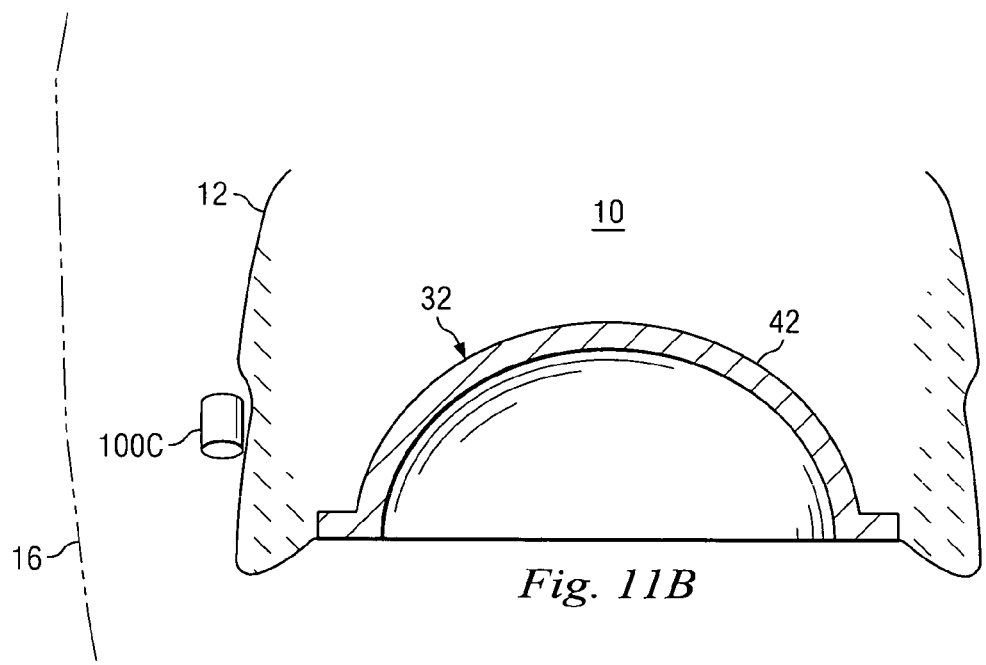
FIG. 11B is the implantable sensor of FIG. 11A shown in a first implanted position.
Figure 11C:
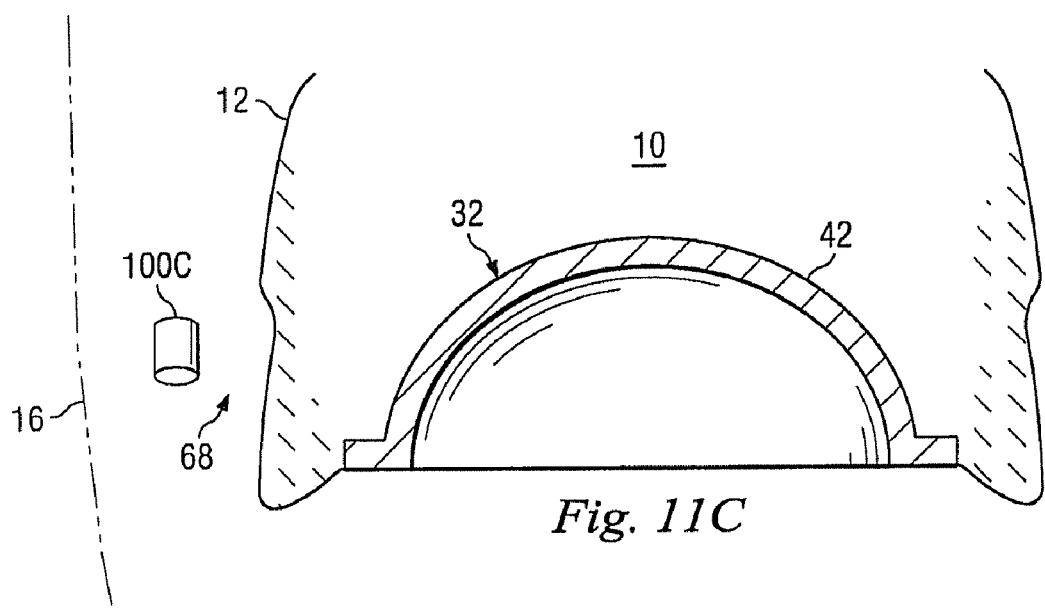
FIG. 11C is the implantable sensor of FIG. 11A shown in a second implanted position.

FIGS. 11A-11C illustrate a possible means of implanting the pedometer 100C according to the present invention. The pedometer 100C may be substantially similar to pedometers 100, 300, 400, 500, 600, 700, and 900 disclosed above. As shown in FIG. 11A and previously described, the pedometer 100C may be shaped for implantation via a catheter 60. Without limitation, it is contemplated that the pedometer 100C may take the shape of an elongated cylinder to facilitate placement via the catheter 60. In one aspect, the diameter is smaller than 4 mm. In another aspect, the diameter may be 3 mm or smaller. Further, the exterior surface of pedometer 100C may include surface irregularities, such as ridges, barbs, knurling, bristle, in-growth texturing, etc., to anchor the sensor in position. Alternatively, or in combination, the outer surface of the sensor may be coated with chemical or biologic agents for promoting adhesion to the adjacent tissue and/or growth of the tissue onto the surface of the sensor. The catheter 60 includes a proximal portion 62 adapted for being disposed outside of the patient's skin 16 and a distal portion 64 adapted for being disposed adjacent the implantation site 18 for the pedometer 100C. Pedometer 100C may be positioned within the proximal portion 62 of the catheter 60 and then moved to the implantation site 18 by shaft 66. Shaft 66 is adapted to force the pedometer 100C through the catheter 60 to the implantation site 18. The distal portion 64 of the catheter 60 may be shaped for accurate placement of the pedometer 100C.

FIG. 11B shows the pedometer 100C disposed adjacent to and in contact with the exterior bone surface 12 of bone 10. While the pedometer 100C is shown adjacent to the bone, it is contemplated that all or only a portion of the sensor may be implanted within the bone. Still further, as with all the pedometers of the present invention, it is contemplated that pedometer 100C may be disposed adjacent a bone the joint to be monitored, within the bone, near the joint, or distal to the joint. FIG. 11C shows the pedometer 100C disposed near, but spaced from, the exterior bone surface 12 as shown by space 68. Depending on the indicators being detected by the sensor of the pedometer 100C, it is contemplated that the pedometer may be located anywhere from a millimeter to several inches away from the exterior bone surface when disposed near the joint. When the pedometer 100C is disposed distal to the joint being monitored, it is contemplated that the pedometer may be located up to several feet away from the joint being monitored. For example, where the pedometer is adapted to detect indicators of steps taken the pedometer may be located within a region of the foot to monitor use of the hip joint.

Figure 12A:
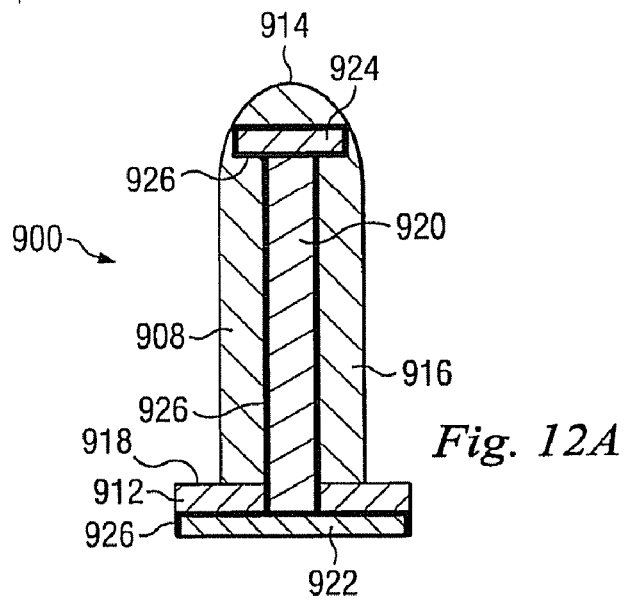
FIG. 12A is an enlarged cross-sectional view of an implantable sensor according to one embodiment of the present invention.
Figure 12B:
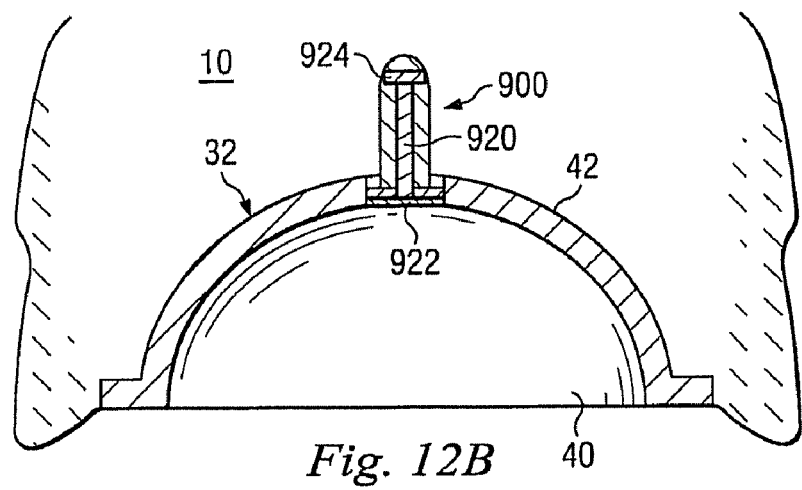
FIG. 12B is a cross-sectional view of the implantable sensor of FIG. 12A engaged with a portion of an implanted hip prosthesis.

FIGS. 12A-12B show a pedometer 900 according to one embodiment of the present invention that utilizes impedance to monitor implant usage. Pedometer 900 may be substantially similar to other embodiments of the present invention. Pedometer 900 includes a main body 908. A head 912 of the pedometer 900 includes a flange portion 918. A leading end 914 of the pedometer 900 is adapted for being disposed within bone. To facilitate bone engagement the pedometer 900 includes threads 916. The threads 916 are configured such that the pedometer 900 may act as a bone screw. The pedometer 900 also includes housing 920. The housing 920 is adapted for storing the electronics of the pedometer 900, such as the integrated circuit, battery, data processor, memory, and communication devices. The housing 920 is insulated from any metal material of the main body 908, head 912, and leading end 914 by an insulator 926 to protect the electronics and allow the pedometer 900 to function properly. The electronics are in communication with electrodes 922 and 924. It is contemplated that electrodes 922 and 924 may be ring, band, or any other type of electrode capable of measuring impedance. Electrodes 922 and 924 are also insulated from any metal material of the main body 908, head 912, and leading end 914 of the pedometer 900 by insulator 926. The pedometer 900 and its electronics are adapted for measuring the impedance between electrodes 922 and 924.

It is contemplated that the electrodes 922 and 924 may be located completely within the main body 908, head 912, and leading end 914 of the pedometer. However, as shown it is also contemplated that the electrode 922 may extend beyond the boundaries of the head 912. In this respect, the electrode 922 may be insulated from the acetabular cup 32 as well as the metal portions of the pedometer 900 itself, but exposed to the space underneath inner surface 40 where the ball-in-socket motion of the artificial hip joint occurs. The fluidic environment of this space contributes to the electric impedance between electrodes 922 and 924. The ball-in-socket motion of the hip joint will modulate the electric impedance between electrodes 922 and 924. This modulated signal can be used as a pedometer to track use of the implant. As in other embodiments, it is contemplated that pedometer 900 may store the implant usage data for later retrieval or may simply immediately communicate the data to an external device. It is also contemplated that a plurality of impedance pedometers may be used.

As briefly described previously, it is contemplated that the sensors according the present invention may utilize a variety of alternative techniques to power the sensor. For example, it is fully contemplated that the sensor may be piezoelectric. It is also contemplated that the sensor may simply use the kinematics of the body for power. For example, the sensor may utilize a MEMS device capable of incrementing a counter in response to a movement of the body meeting a threshold.

While the foregoing description has been made in reference to a hip joint, it is contemplated that the disclosed pedometers and sensors may have applications throughout the body. Specifically, such disclosed sensors may be useful to evaluate movement and detect changes to natural and artificial joints such as, but not limited to, the knee, spine, shoulder, elbow, jaw, ankle, wrist, and fingers. Moreover, the acoustic sensor may also be used to listen for changes in bodily systems and organs and alert healthcare professionals to any impending problems.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. An implantable pedometer for measuring use of a joint in a skeletal system, comprising:
    an elongated housing having an external surface, at least a portion of the external surface configured for bone engagement;
    an acoustic sensor disposed within the housing, the sensor adapted for detecting a sound indicative of joint use;
    a memory unit disposed within the cylindrical housing and in communication with the sensor, the memory unit adapted for storing a count data corresponding to the number of sounds indicative of joint use detected; and
    a telemetry circuit configured for transmitting the count data outside of the skeletal system.

2. The pedometer of claim 1, wherein the sensor is adapted for engaging a bone of the joint.

3. The pedometer of claim 1, wherein the external surface includes a fixation projection.

4. The pedometer of claim 3, wherein the fixation projection includes bone screw threads.

5. The pedometer of claim 1, wherein the joint is an artificial joint.

6. The pedometer of claim 5, wherein the sensor is adapted for being disposed adjacent to the artificial joint.

7. The pedometer of claim 5, wherein the sensor is adapted for being disposed distal to the artificial joint.

8. The pedometer of claim 5, wherein the artificial joint is one of the following an ankle, a knee, a hip, a spinal portion, a shoulder, an elbow, a wrist, or a jaw.

9. The pedometer of claim 5, wherein the external surface includes a means for attaching to the artificial joint.

10. The pedometer of claim 9, wherein the means for attaching to the artificial joint is a threaded connection.

11. An implantable pedometer for measuring use of a joint in a skeletal system, comprising:
    an acoustic sensor adapted for detecting an indicator of joint use
    a counter for storing a count data corresponding to the number of indicators detected;
    a telemetry circuit configured for transmitting the count data outside of the skeletal system; and an elongated housing for holding the acoustic sensor, the counter, and the telemetry circuit.

12. The pedometer of claim 11, wherein the acoustic sensor includes a piezoelectric transducer.

13. The pedometer of claim 11, wherein the joint is one of a spinal portion, a shoulder, an elbow, a wrist, or a jaw.

14. The pedometer of claim 11, wherein the acoustic sensor includes a microphone.

15. The pedometer of claim 14, wherein the pedometer further includes a recording device in communication with the microphone.

16. The pedometer of claim 15, wherein the recording device operates using a buffer.

17. The pedometer of claim 11, wherein the joint is one of a hip, a knee, or an ankle.

18. The pedometer of claim 17, wherein the indicator is a sound.

19. The pedometer of claim 18, wherein the sound is associated with stepping.

20. An implantable pedometer for measuring use of a joint in a skeletal system, comprising:
a single elongated pedometer housing adapted for containing all components of the pedometer;
a sensor disposed within the pedometer housing, the sensor adapted for detecting indicators of joint use and storing a count data corresponding to the number of indicators detected; and
a telemetry circuit disposed within the housing, the telemetry circuit configured for transmitting the count data outside of the skeletal system.

21. A method of using an implantable pedometer to evaluate use of a joint in a body, comprising:
implanting a programmable sensor into the body, the sensor adapted for detecting indicators associated with use of the joint, storing a usage data corresponding to the number of indicators detected that satisfy a threshold, and modifying the threshold based on an external input;
obtaining the usage data from the sensor; and
analyzing the usage data to evaluate the amount of use of the joint.

22. The method of claim 21, further comprising modifying the threshold based on an external input.

23. The method of claim 22, wherein the indicators correlate to movements related to use of the joint.

24. The method of claim 23, wherein the usage data is a representation of the number of movements made.

25. The method of claim 23, further comprising analyzing the usage data by spectral analysis.

26. The method of claim 23, wherein the sensor is further adapted for distinguishing between different types of movements.

27. The method of claim 26, wherein the usage data is grouped by the different types of movements.

28. The method of claim 22, wherein the joint is an artificial joint.

29. The method of claim 28, wherein the sensor is implanted during the same surgical procedure as the artificial joint.

30. The method of claim 29, wherein the sensor is attached to a portion of the artificial joint prior to being implanted.

31. The method of claim 28, wherein the sensor is implanted in a surgical procedure separate from the surgical procedure used to implant the artificial joint.

32. The method of claim 31, wherein the sensor is implanted percutaneously.

33. An implantable pedometer for measuring use of an artificial hip implant within a patient, the pedometer comprising:
an elongated housing adapted for implantation through a catheter and separate from the artificial hip implant, the housing having an external surface configured for tissue engagement;
an acoustic sensor disposed within the housing, the acoustic sensor configured for detecting an acoustic indicator of the patient taking a step;
a memory unit disposed within the housing and in communication with the acoustic sensor, the memory unit for storing a count data corresponding to the number of indicators detected; and
a telemetry circuit configured for transmitting the count data outside of the skeletal system.

34. The pedometer of claim 33, further comprising a power source disposed within the housing and connected to the acoustic sensor and the memory unit.

35. The pedometer of claim 34, wherein the power source is a rechargeable battery.

36. The pedometer of claim 34, wherein the power source is rechargeable wirelessly.

37. The pedometer of claim 34, further comprising a signal processor disposed within the housing and in communication with the acoustic sensor and the memory unit, the signal processor for determining whether a detected acoustic signal is an indicator of the patient taking a step.

38. The pedometer of claim 37, wherein the telemetry circuit includes an antenna.

39. The pedometer of claim 37, wherein the telemetry circuit includes a coil adapted for inductive coupling.

40. The pedometer of claim 37, wherein the count data stored by the memory unit is a scaled representation of the number of indicators detected.

41. The pedometer of claim 40, wherein the memory unit is adapted to be reset to clear the count data.

42. The pedometer of claim 37, wherein the external surface is configured for being disposed in a bony tissue adjacent to the artificial hip implant.

43. The pedometer of claim 42, wherein the external surface includes a anti-migration structure to provide a secure engagement between the housing and the bony tissue.

44. The pedometer of claim 37, wherein the external surface is configured for being disposed in a soft tissue adjacent to the artificial hip implant.

45. The pedometer of claim 44, wherein the wherein the external surface includes a anti-migration structure to prevent unwanted movement between the housing and the soft tissue.

46. The pedometer of claim 37, wherein the signal processor determines whether the detected acoustic signal satisfies a predetermined parameter indicative of the patient taking a step.

47. The pedometer of claim 46, wherein the predetermined parameter is selected from the group consisting of an amplitude range, a frequency range, and a decibel range.

48. The pedometer of claim 46, wherein the signal processor is programmable to set the predetermined parameter.

49. The pedometer of claim 48, wherein the signal processor is programmable wirelessly.

* * * * *